(12) United States Patent
Shigemori et al.

(10) Patent No.: US 6,541,227 B1
(45) Date of Patent: Apr. 1, 2003

(54) PREPARATION OF LABELED DNA

(75) Inventors: Yasushi Shigemori, Kisarazu (JP);
Atsushi Hattori, Ichikawa (JP)

(73) Assignee: Aisin Seiki Kabushiki Kaisha, Kariya (JP)

( * ) Notice: Subject to any disclaimer, the term of this patent is extended or adjusted under 35 U.S.C. 154(b) by 0 days.

(21) Appl. No.: 09/416,063

(22) Filed: Oct. 12, 1999

(30) Foreign Application Priority Data

| Oct. 12, 1998 | (JP) | ............................................ 10-303234 |
| Jan. 22, 1999 | (JP) | ............................................ 11-013986 |
| Mar. 19, 1999 | (JP) | ............................................ 11-076430 |

(51) Int. Cl.⁷ ............................ C12P 19/34; C12N 9/10; C12N 15/11
(52) U.S. Cl. ........................ 435/91.5; 435/193; 536/23.1
(58) Field of Search .......................... 435/6, 91.2, 91.5, 435/193; 536/23.3, 23.1

(56) References Cited

U.S. PATENT DOCUMENTS

| 4,689,405 A | 8/1987 | Frank et al. .................. 536/27 |
| 5,670,316 A | * 9/1997 | Sena et al. ..................... 435/6 |
| 5,744,305 A | 4/1998 | Fodor et al. .................... 435/6 |

OTHER PUBLICATIONS

Golub et al;., "Inhibition of RNA polymerase II transcription by oligonucleotide–RecA protein filaments targeted to promoter sequences" Proc. Natl. Acad. Sci. USA, vol. 90, pp. 7186–7190, 1993.*

* cited by examiner

*Primary Examiner*—John S. Brusca
(74) *Attorney, Agent, or Firm*—Burns, Doane, Swecker & Mathis, LLP

(57) ABSTRACT

A preparation method of labeled DNA and use thereof are disclosed. More specifically, the invention relates to a preparation method of labeled DNA by preparation of a complex triple-stranded DNA through an deoxyoligonucleotide complementary to the deoxyoligonucleotide sequence of the 3' terminal sequence of a certain double-stranded DNA followed by replacement of the 3' terminal region of the plus strand of said double-stranded DNA with at least one labeled dNTP, and also to said immobilization method of a DNA obtained from the preparation method of the labeled (or modified) DNAs onto a solid support. These subject matters are mainly useful for preparation of labeled DNA molecules.

12 Claims, 21 Drawing Sheets

Autoradiography

Photography

Autoradiography

Photography

Autoradiography

Autoradiography

Autoradiography

Photography

Autoradiography

Photography

Autoradiography

Photography

Autoradiography

Photography

Autoradiography

Photography

Autoradiography

Photography

Autoradiography

Photography

Autoradiography

Photography

Autoradiography

Photography

Autoradiography

Photography

Autoradiography

Photography

Autoradiography

Photography

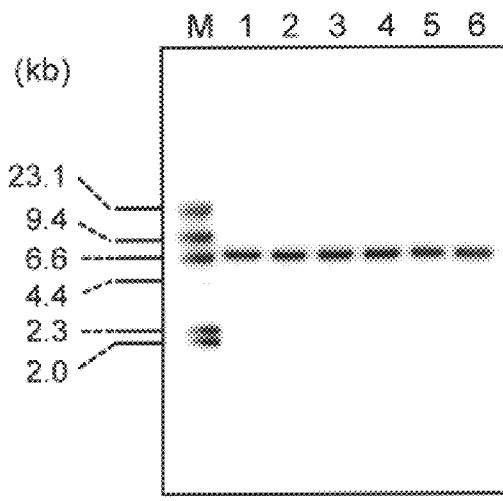
*Fig. 19A* Autoradiography
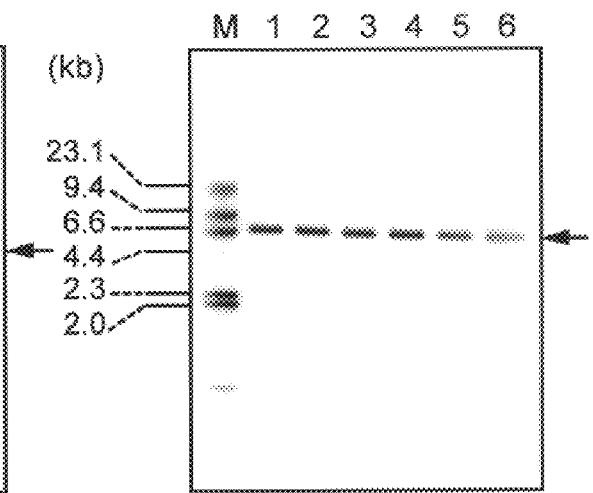
*Fig. 19C* Autoradiography
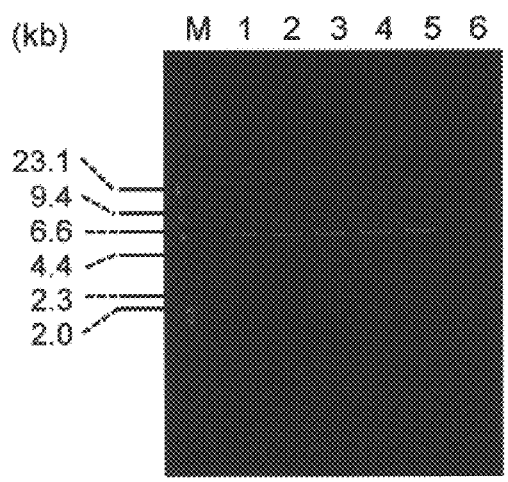
*Fig. 19B* Photography
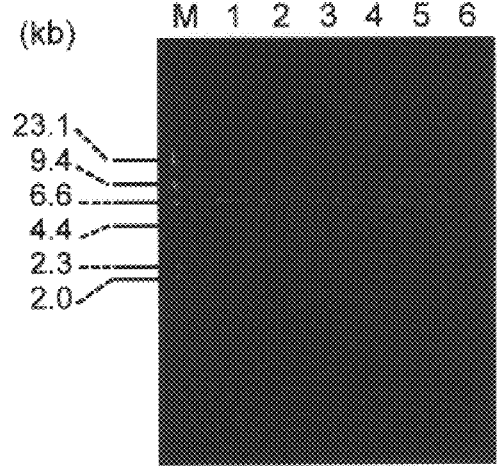
*Fig. 19D* Photography

PREPARATION OF LABELED DNA

BACKGROUND OF THE INVENTION

1. Field of the Invention

The present invention belongs in general to a technical field related to modification of DNA molecules, and relates to a preparation method of labeled DNA and use thereof. More specifically, the present invention relates to a novel preparation method of labeled DNA by substituting an deoxyoligonucleotide sequence of a certain part of at least one of two single-stranded DNAs constructing a certain double-stranded DNA molecule with an deoxyoligonucleotide having at least one labeled nucleotide. Moreover, the present invention relates to use of the labeled DNA molecule for direct cloning and direct probing of DNA fragments, as well as to an immobilization method of said labeled DNA molecule onto a solid support.

2. Description of the Related Art

Labeled DNA molecules are widely used, for example, as a means to specifically detect a certain DNA, a nucleotide sequence of a certain region in the DNA and the like, that is they are used as probes in technical fields such as biochemistry, medicine, health care and the like. As typical preparation methods of such a probe, (a) nick translation method, (b) random primer DNA labeling method, (c) DNA terminal labeling method using T4 polynucleotide kinase, and (d) incorporation method of labeled nucleotides into a PCR product using PCR can be mentioned. However, among those methods, whereas a single labeled nucleotide can be incorporated into a high molecular weight DNA of interest at the terminal of the DNA molecule by (c), the incorporating efficiency becomes low. Thus, (c) has a disadvantage in that it is difficult to improve the sensitivity (specific activity) of the probe. Further, because of the feature of the method to use random primers, the required length of DNA fragment to be labeled in (b) is at least 500 bp (mer) and when using a shorter DNA than those, short fragments tend to be dominantly produced (for example, Harrison B. et al., Anal. Biochem. 1986, 158 (2): 307–315). On the other hand, although with either of (b) and (c) labeled nucleotides can be incorporated into a DNA of interest at a high efficiency to achieve a high specific activity, it is difficult to obtain a probe with a certain strand length by those methods (for example, see Feinberg AP, et al., Anal. Biochem. 1983, 132 (1); 6–13 for (b)). Moreover, (a) is, in a simple form to mention, a method having an action where nicks are made within a double-stranded DNA molecule by cutting it with a suitable endonuclease, the nicked DNA strand is digested with a 5'→3' exonuclease, and the digest is replaced with a new DNA strand using a polymerase activity. Whereas this method allows to increase the specific activity, the incorporation rate of nucleotide labeled through a long-term reaction is decreased in general and it is not easy to obtain a probe with a certain strand length through the method.

In addition, with each of the above-mentioned methods of (a), (b) and (c), as all types of the DNA molecules contained in a DNA containing sample is in general to be the DNA subjected to be labeled, it is essential to individualize the DNA molecules of interest when multiple types of DNA molecules present in the sample.

As a certain embodiment to use the above-mentioned DNA probe, DNA tips can be mentioned. DNA tips (or DNA microarraies) have been proposed to be a potent means for analysis of gene expression, mutation, polymorphism and the like, and some of them have been in their practical use.

As preparation processes of such DNA tips, a method where the surface of a solid support is firstly treated to bare a positive electric charge and then a DNA is directly immobilized onto the solid support electrostatically, or a synthetic deoxyoligonucleotide is immobilized onto a solid support through covalent binding, or a DNA is directory synthesized on the surface of a solid support (for example, U.S. Pat. Nos. 4,689,405; 5,744,305) has been known. Although each of these methods has its merits and demerits, they are chosen to suite the purpose of use.

For example, to investigate gene expression, cDNA and a part of which, that is a polynucleotide of approximately 200–300 bp, is used for immobilization, and these polynucleotides are generally prepared by PCR amplification using a genome or cDNA library as its template. Moreover, a method where, when the PCR is conducted, biotin or a primer modified with amino group is used to obtain a DNA with the labeled 5' terminus, and through the terminus of thus prepared DNA, immobilization of the DNA is conducted has been proposed. However, if a number of labeled DNA are to be prepared by PCR to generate a DNA microarray which prerequisite is to align multiple DNA molecules on a solid support, it will be tedious and expensive. Furthermore, because of difference in nature of enzymes (thermostable enzymes) used in PCR method, there is a possibility that some bases in the PCR product (DNA) will be altered, and one must confirm the sequence of said PCR products. In addition, terminal-labeled DNAs prepared with the PCR method have their 5' terminal labeled. Thus, when a DNA tip is generated using them, it has a structure where its 5' terminal of the DNA is oriented to the solid surface. In some applications, such a structure is inconvenient. For example, when cDNA synthesis or RNA synthesis, or the following protein synthesis is conducted on a DNA tip, a structure where the 3' terminus of the DNA is oriented to the solid surface is essential.

On the other hand, when DNAs are directly synthesized on a solid support, conveniently at most only 100 bp of DNA can be immobilized. Moreover, with a method where DNAs are statistically immobilized on a solid support, it is difficult in general to increase the density of the DNA array. In addition, it is difficult to submit thus obtained DNA array for repeating use, because the associating strength of the DNA to the solid support is weak. Moreover, because of the DNA structure which is allowed on the DNA array, stable hybridization is difficult to be achieved.

According to conventional art relating to introduction of a label (or a certain binding group for modification) into a certain region of a polynucleotide, even if it is a prerequisite only to provide a DNA detection probe, only the probe which is likely to reduce the detection accuracy of a target DNA will be obtained due to irregularity in length of the resulting labeled DNA molecules.

Accordingly, it will need to obtain a method where DNA molecules with any length can be selectively labeled or modified, and also where a nucleotide able to specifically label or modify only a certain nucleotide sequence among said molecules with a high efficiency can be provided.

SUMMARY OF THE INVENTION

The present inventors have been searching for a method to efficiently modify or label DNAs with a label (which comprises a group or a portion which can form a biological, specific bond, or form a chemical, covalent bond). As a result, it was found that nucleotides which have been labeled with variety types of probes can be efficiently introduced in a certain place of a target DNA in accordance with a reaction which is similar to homologous recombination (or it is called as "generalized recombination") which is considered to progress through complex formation of a single-stranded-DNA with a double-stranded DNA. More specifically, it was found that a target double-stranded DNA fragment (molecule) and a single-stranded DNA (deoxyoligonucleotide) homologous to a nucleotide sequence of a certain region thereof form a triple-stranded DNA, and then when a reaction of a 3'→5' exonuclease is conducted under the existence of four types of dNTPs including at least one labeled dNTP, along with or before a reaction of a 5'→3' polymerase, a certain region of at least one of the two single-stranded DNAs constructing the double-stranded DNA, the region corresponding to the deoxyoligonucleotide, can be replaced by the nucleotide sequence containing the labeled nucleotide. The invention is based on such findings.

Accordingly, the above-mentioned objective can be achieved by a method according to the invention, where a labeled double-stranded DNA molecule is prepared by replacing an deoxyoligonucleotide sequence of a certain region of at least one of the two single-stranded DNAs constructing a certain double-stranded DNA molecule with an deoxyoligonucleotide sequence having at least one labeled (or modified with a binding group), and the labeled single-stranded DNA molecule is separated and obtained if necessary. Such a method comprises the steps of:

(A) incubating at least one type deoxyoligonucleotide having a sequence substantially homologous to said one of the deoxyoligonucleotide sequence of at least one of a certain part with said double-stranded DNA molecule under a condition where said deoxyoligonucleotide and double-stranded DNA molecule can partially form a triple-stranded DNA, and (B) incubating at least one type of complexes in the presence of four types of dNTPs comprising at least one labeled dNTP under a condition where an deoxyoligonucleotide sequence of a certain region of at least one of the two single-stranded DNAs constituting the double-stranded DNA molecule among the complex can be substituted with the deoxyoligonucleotide sequences having at least one labeled nucleotide (the above method is referred as to a basic preparation method hereinafter).

Moreover, according to the invention, as one of the embodiments where the above-mentioned preparation method is used, when immobilizing DNAs onto a solid support, use of DNAs which are labeled (or modified) with a binding group and can be prepared by the method above is also disclosed. Specifically, a method for immobilization of a target DNA labeled with a member of binding partners onto a solid support on which surface another member of the binding partners is supported by forming a bond between said members, wherein the DNA immobilization method is characterized in that said labeled target DNA is prepared by the steps of:

(A) forming a triple-stranded DNA between a double-stranded DNA consisting of a target DNA and a basic sequence complementary to said DNA, and an deoxyoligonucleotide having a sequence substantially homologous to a part of an deoxyoligonucleotide sequence of the target DNA, and (B) replacing said deoxyoligonucleotide of a part of the target DNA with an deoxyoligonucleotide having at least one labeled nucleotide in the presence of dNTP comprising at least one dNTP labeled with said member of the binding partners by using thus obtained triple-stranded DNA, is provided (which is referred as to an immobilization method hereinafter).

An deoxyoligonucleotide sequence of a certain region or a part of the deoxyoligonucleotide in said double-stranded DNA may be located at the 3' terminal side of the double-stranded DNA or in its non-terminal region. As referred in the invention, "non-terminal region" is, as long as in accordance with objectives of the invention, a region which is not comprise the nucleotide of the both termini of the double-stranded DNA, and in the case of a circular double-stranded DNA it may be any region, and in the case of a straight double-stranded DNA, it means the middle region and other suitable regions which do not includes nucleotides at its both termini.

In the above-mentioned basic preparation method, even under conditions where a certain double-stranded DNA molecule coexists with other double-stranded or single-stranded DNA molecules, substitution of a nucleotide sequence can be conducted selectively using a certain double-stranded DNA molecule as the target. Moreover, according to said preparation method, a nucleotide sequence to be replaced in the double-stranded DNA molecule is substantially restricted to a part corresponding to the deoxyoligonucleotide (a single-stranded DNA) used to form the triple-stranded DNA as a complex. In addition, according to the above-mentioned preparation method, a certain (or target) double-stranded DNA molecule, if its length is longer than that of the deoxyoligonucleotide used to form a triple-stranded DNA, can theoretically replace the above-mentioned nucleotide sequence with any length. Moreover, according to the above-mentioned preparation method, by choosing types or amounts of the labeled dNTP used in the process (B), the labeled double-stranded DNA comprising a desired label at a desired content can be obtained.

Accordingly, as a further embodiment of the invention, a DNA probing composition consisting of a labeled double-stranded DNA molecule obtained in the above-mentioned preparation method or of a labeled single-stranded DNA molecule obtained from said double-stranded DNA molecule; and a composition for direct gene cloning comprising of said labeled double-stranded DNA molecule, and a method to detect DNA fragments are provided.

As a further alternative embodiment of the invention, a detection method of DNA fragments having an deoxyoligonucleotide sequence of a certain region homologous to an deoxyoligonucleotide used in the above-mentioned preparation method which is characterized in that said preparation method is conducted in an aqueous solution comprising a variety of DNA fragments is also provided.

On the other hand, according to the immobilization method, as an other certain embodiment of the invention, a DNA tip where at least one target DNA is immobilized onto a solid support, wherein the DNA tip is formed by a binding between the solid support, on which surface a sort of avidin is supported and the target DNA labeled with a sort of biotin through a complex formation between the biotin and the avidin is also provided.

According to such an immobilization method, by choosing an deoxyoligonucleotide used to form a triple-stranded DNA, only a region of a nucleotide sequence substantially homologous to said deoxyoligonucleotide in a desired region of the target DNA can be specifically replaced with the deoxyoligonucleotide sequence containing at least one nucleotide labeled with a member of the binding partners, and through the member thus introduced into the target DNA the target DNA can be immobilized onto a solid support supporting another member of the binding partners in a desired way.

When such an immobilization method is used, a DNA microarray (or a DNA tip) where a DNA with a desired strand length is immobilized onto a solid support with a desired association strength and an extremely high density can be provided.

BRIEF DESCRIPTION OF THE DRAWINGS

FIGS. 19A, B, C and D respectively are autoradiographs (A nd C) and photographs (B and D) showing electrophoretical behavior on a gel submitted to autoradiography or stained with ethidium bromide after agarose gel electrophoresis, as conducted in Example 16.

(a) is a phase where the target DNA subjected to biotin-labeling reaction is bound onto the sensor surface to which streptoavidin has been bound. (b) is a phase where the immobilized double-stranded DNA is dissociated into single-stranded DNAs by alkaline denaturation, followed by replacement of the buffering solution in the cuvette with 6×SSC. (c) is a phase where a single-stranded DNA complementary to the target DNA is added. (d) is a phase where the single-stranded DNAs are removed by alkaline denaturation, followed by replacement of the buffering solution in the cuvette with 6×SSC. (e) is a phase where a single-stranded DNA having the sequence unrelated to the target DNA is added. (f) is a phase where a single-stranded DNA complementary to the target DNA is added.

DETAILED DESCRIPTION OF THE PREFERRED EMBODIMENTS OF THE INVENTION

"Double-stranded DNA molecule" and "deoxyoligonucleotide" in the above-mentioned basic preparation method are considered to correspond to "double-stranded DNA" and "deoxyoligonucleotide" in the immobilization method, respectively.

Figure 1:
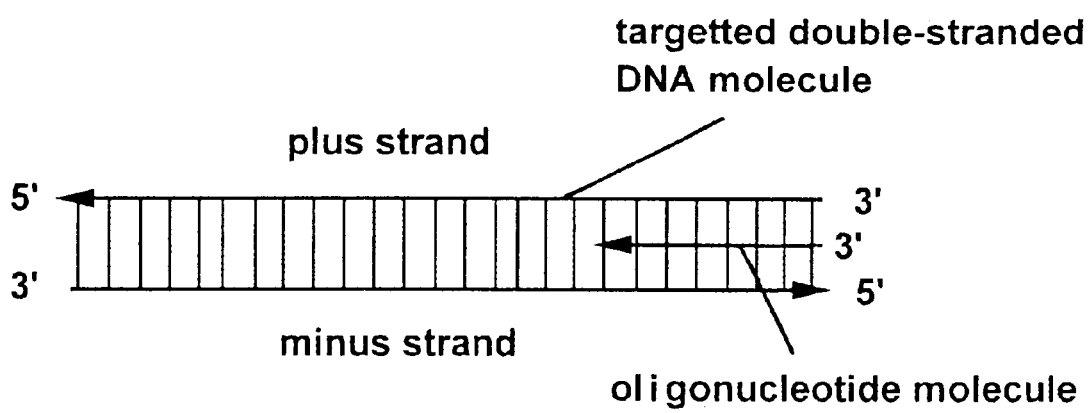
FIG. 1 is a schematic diagram of a double-stranded DNA molecule used as a target in the invention. This figure shows the relationship between an deoxyoligonucleotide molecule and said double-stranded DNA molecule to form a triple-strand, along with the direction of the sequence and the parts of the sequence.

In this invention and this specification, the prefix "oligo" when referred "deoxyoligonucleotide" is mainly used with an intention to discriminate the length of the double-stranded DNA to be labeled from that of the single-stranded DNA used to form triple-stranded DNAs, and is generally used to include the notion of "poly" without sticking to the notion of "oligo" commonly recognized in this art. Moreover, the term "DNA molecule" herein referred has a notion including also DNA fragments, and excluding DNA existing in an organism. Further, "3' terminal region" of "a certain region" or "a part of the target DNA" herein referred means one or both of 3' terminal region of the plus strand or the minus strand when a double-stranded DNA is drawn in a schematic diagram such as FIG. 1. On the other hand, "non-terminal region" (or non-terminal part) is, as described earlier, a region which does not include at least one nucleotide of the both termini of a double-stranded DNA in accordance with the objectives of the invention. Accordingly, in the case of a closed circular DNA molecule which has no terminus, it can be in any region thereof, and in the case of a straight double-stranded DNA molecule, it can be any region including the middle region and other regions which do not include at least one nucleotide at the both ends. But from the view point to form a stable triple-stranded DNA, a region where a double-stranded DNA suffers from a stress, for example a region where super (higher order) helix structure is formed, a twisted part of the structure due to DNA topoisomerase activity can be mentioned as specified examples of the non-terminal regions. Although aiming at simplifying the illustration, replacement of 3' terminal region of a plus strand is explain as examples hereinafter, it should be understood that the invention is not limited to these.

A double-stranded DNA (or a target DNA) referred in the invention, may be any DNA fragment regardless of its origin and length as long as it can be replaced with the deoxyoligonucleotide labeled according to the above-mentioned preparation method. For example, any artificial synthetic DNA, as well as any DNA fragment derived from any species of prokaryote and eukaryote can be encompassed in the category of double-stranded DNA, when it has a technical significance to be labeled (for example, as a probe). To add further explanation about the double-stranded DNAs, and DNAs derived from human, monkeys, mice or rats, for example, double-stranded DNAs having the whole or a part of the gene which can be related to any disease can be mentioned, and also an artificial DNAs, for example, double-stranded DNAs synthesized using a DNA autosynthesizer and the like which commonly used in the art can be mentioned. These DNAs may be in general of 100 bp or larger, and more specifically of from 500 bp to 50 kbp. When such DNAs became the objects, the preparation method of the invention will be useful in the field of health care or biochemical research.

Furthermore, the invention of the immobilization method which utilizes such a preparation method will be useful to investigate for example gene expression, mutation, polymorphism and the like. Now, such double-stranded DNA molecules will contain new and sequence-nonspecific nucleotide sequences in some cases such as when nicks exist in the molecule, so it is preferable to avoid to have target double-stranded DNA with nicks.

In the above-mentioned preparation method, a triple-stranded DNA complex is formed using an deoxyoligonucleotide having a sequence substantially homologous to the 3' terminal region or a non-terminal region of a plus strand of the above double-stranded DNA molecule. Moreover, in other word to say according to the illustration of the immobilization method, a triple-stranded DNA complex is formed between a double-stranded DNA consisting of a target DNA and a basic sequence complementary to said DNA, and an deoxyoligonucleotide having a nucleotide sequence substantially homologous to a part of regions of the target DNA in process (A).

When such triple-stranded DNA complexes (or referred as to simply "triple-stranded DNAs") are formed, an deoxyoligonucleotide having a sequence substantially homologous to the nucleotide sequence of the 3' terminal region or a non-terminal region of the minus strand of the double-stranded DNA can be used independently or at the same time.

The term "substantially homologous" means that said deoxyoligonucleotide and double-stranded DNA can form a triple-stranded DNA at the 3' terminal region or the non-terminal region of the double-stranded DNA and that the deoxyoligonucleotide may contain a few different nucleotides to the extent that said nucleotide sequence can be replaced with a new nucleotide sequence according to the invention. As such an extend, although it can not be defined because it will change depending on the length and location of the deoxyoligonucleotide, the cases where usually a few (from two to four) nucleotides at the proximity of the 5' and 3' termini of the deoxyoligonucleotide and one nucleotide at the central region differ(s) from the nucleotide sequence of the corresponding double-stranded DNA can be mentioned. However, from the view point to conduct an accurate replacement of the nucleotide sequence, use of an deoxyoligonucleotide completely homologous to the corresponding nucleotide sequence of the target double-stranded DNA molecule is preferred.

The length of such deoxyoligonucleotides needs not specifically defined as long as they can form triple-stranded DNA in the manner descrived above. But when a triple-stranded DNA is formed in an aqueous solution containing a homologous recombinant protein which is a preferred embodiment of the invention, an deoxyoligonucleotide with the length of at least 15 mer or 20 mer is used depending on the type of the homologous recombinant protein. The length is preferably 30 mer or longer, more preferably 40 mer or longer, and although theoretically there is no upper limitation, the maximum length in practical use is up to 150 mer.

Homologous recombinant proteins which can be used in the preferred embodiment above may be any protein regardless of its origin as long as a target double-stranded DNA molecule and said deoxyoligonucleotide can form a stable complex through said protein when it exists. Still, as specified examples of such proteins, recA protein derived from *Escherichia coli*, multi-functional proteins which are encoded by recA gene in a heat-resistant bacteria (*Thermus thermophilus*) and other enteric bacterium, and recA like proteins which are know per se derived from *Agrobacterium tumfaciens, Bacillus subtilis, Methylophilus methylotrophus, Vibrio cholerae, Ustilago maydis* and the like can be mentioned. Other than those, recA like proteins derived from an yeast (*Saccharomyces cerevisiae*) and recA like protein (Rad 51 protein) derived from human are included in said homologous recombinant proteins. Among those, it is preferable to use recA protein derived from *E. coli* or the proteins having the similar functions to that thereof (for example, modified protein or fragment thereof derived from said protein) from the view point of availability and stability. As modified proteins, recA gene product crated from site-specific mutagenesis of recA gene, wherein it is constituted with an amino acid sequence with one or more amino acid(s) deleted, replaced or added and has functions to form a complex having the above-mentioned triple-stranded DNA part like recA protein does, can be mentioned. In those with some amino acids deleted, proteins or peptides comprising a binding domain of recA protein directed to a single-stranded DNA are included. As examples of such peptides, those described by Voloshin et al., in Science, Vol. 272, 1996: 868–872, can be mentioned. And as it can be understood hereinabove, the term of protein referred in the invention is used in accordance with a notion where it also includes peptides.

When using a homologous recombinant protein in formation of a complex comprised of the three components of a double-stranded DNA, an deoxyoligonucleotide and said protein, adenosine 5'-triphosphate (ATP) or its analogues, such as adenosine (γ-thio)triphosphate (ATP-γS), or DATP, UTP, dUTP, CTP, dCTP, GTP or the like will be needed. At least one or more of those nucleotide triphosphates or those analogues is/are used and in some cases nucleotide diphosphates may be included. When physical decomposition of ATP is observed in process (B) in the preparation method of labeled double-stranded DNA molecules as mentioned hereinafter, it is preferred to use the latter ATP-γS to form the complex comprised of the above three components. Here, the abbreviations for the above-mentioned nucleotides are based on those traditionally used in the art.

Those skilled in this art will easily choose the optimal reaction conditions to form such a tree-component complex, depending on recA protein or recA like protein used, by conducting simple experiments according to Examples described hereinafter.

When a tree-component complex is formed using recA protein as mentioned above, the complex may be subject to the following reaction after removal of recA protein from said complex in some cases. Such a removing reaction may be conducted using any non-specific protease as long as it will not have adverse effects on the preparation method according to the invention. Still, Proteinase K derived from *Tritrachium album* can be used conveniently when considering availability and stability. As a proteolytic reaction condition to use Proteinase K, traditional conditions commonly used in the art can be used as they are or with some modifications. For example, Proteinase K is added to a buffering solution consisting of 0.01 M Tris (pH 7.0) and 0.5% SDS at the concentration of 50 μg/ml and then the above-mentioned reaction is conducted under the conditions to incubate the reactants at 37° C. for 10 min.

Even the triple-stranded DNA is obtained after removal of the protein from the above-mentioned three-component complex will still be stable in the above-mentioned enzymatic reaction solution, and can be subjected to the replacement reaction of deoxyoligonucleotide sequence in process (B) according to the invention as it is or after separation if needed. The two types of enzymes above can be of any origin as long as it can exert the effect of interest, and the reaction can be conducted at the coexistence of those enzymes. As those enzymes, at least one type of enzyme chosen from a group consisting of DNA Polymerase I, DNA polymerase Klenow fragment (Klenow enzyme), DNA Polymerase I Klenow fragment (Exominus), T4 DNA Polymerase and T7 DNA Polymerase, and gene-modified polymerases thereof and various types of heat-resistant polymerases can be mentioned. Especially, DNA Polymerase I Klenow fragment (which is referred as to Klenow enzyme hereinafter) can be conveniently used. Klenow enzyme is the one where the 5'→3' exonuclease activity is deleted which locates at the C terminal side of *E. coli* DNA Polymerase I, and shows the 5'→3' polymerase activity and the 3'→5' exonuclease activity in the presence of deoxyribonucleoside triphosphates (dNTPs). Commercially available Klenow enzymes can be use as they are.

Usually, the above-mentioned dNTPs includes the following four types as used; dATP, dCTP, dGTP and dTTP, but when the dNTPs are replaced with at least one of these such as dATP which is partly or totally labeled or another dNTP which is also labeled is used to conduct the above-mentioned reaction, the newly formed nucleotide sequence can include one or more labeled nucleotide(s) therein. The reaction conditions for use of Klenow enzyme are known per se in the art, and it is easy for those of skilled in the art to decide the optimal conditions according to Examples described hereinafter. As specified examples for such conditions, a condition where Klenow enzyme is added at 200 unit/ml to a buffering solution consisting of 0.01 M Tris (pH 7.5), 0.005 M $MgCl_2$, 0.0075 M dithiothreitol and then incubated at 37° C. for 15 min, can be mentioned.

Labels and labeling methods which can be used to label the above-mentioned dNTP are also well-known in the art, and some commercially available labels can be use as they are or newly labeled dNTP may be generated according to the purpose. As such labels, although it is not limited to, but radioisotopes and low molecular weight organic compounds can be mentioned. As a low molecular weight organic compound, not only so-called label but also a drug having any efficacy may be used as long as it can be incorporated into the newly formed nucleotide sequence without exerting any adverse effect on the above-mentioned replacement reaction. As representative labels of this sort, $^{32}P$, $^{35}S$, $^{33}P$, $^{3}H$, biotin, fluorescein, digoxigenin, tetramethylrhodamin, alkaline phosphatase and the like can be mentioned. As examples of deoxynucleoside triphosphate labeled with those labels, [α-$^{32}P$]dATP, [α-$^{32}P$]dCTP, [α-$^{32}P$]dGTP, [α-$^{32}P$]dTTP, biotin-16-dUTP, biotin-11-dCTP, fluorescein-2-dCTP, digoxigenin-11-dUTP, fluorescein-12-dUTP, 6-aminohexyl dATP, tetramethylrhodamine-5-dUTP and the like can be mentioned.

The above-mentioned label corresponds to a member of the binding partners in the immobilization method. "Binding partners" mean members which can mutually form a bond, and it is not matter if they are functional groups, parts of a molecule or residues when they can immobilize a target DNA onto a solid support, which is one of objectives of the invention. Generally, the binding partners are functional groups, parts of a molecule or residues which can mutually form a biological, specific bond, or functional groups, parts of a molecule or residues which can form a chemical, covalent bond, and such a covalent bond may be the one which is formed through a spacer derived from for example a bifunctional organic compound.

As the binding partners to form a biological, specific bond, they are not limited to, but combinations such as a sort of biotin—a sort of avidin, antigen (or antigen determinant)—antibody, oligosaccharide—lectin, and the like can be mentioned. When a solid support made according to the method of the invention on which a DNA is immobilized is used as a DNA tip, it is suitable to choose the binding partners of a sort of biotin—a sort of avidin in that the bond has a certain level of binding strength so that it can be subjected to the repeated use for the following hybridization process with a high accuracy, and the solid support can be subjected to recycle used because the immobilized DNA can be easily peeled off therefrom.

As a sort of biotin, biotin, biocytin, desthiobiotin, oxybiochin, or derivatives thereof which can form a stable complex with avidin can be mentioned. "Ability to form such a stable complex" means the ability to form a complex having a dissociation constant similar to that of biotin—avidin complex ($10^{-15}$ M). On the other hand, as a sort of avidin, avidin, streptoavidin, or modified versions thereof which can form a stable complex with biotin can be mentioned. "A stable complex" in this regard is a synonym defined for a sort of biotin above. And modified versions mean modified compounds or fragments of naturally-occurred avidin or streptoavidin, or recombinants thereof.

For functional groups, parts of a molecule or residues which can form a chemical, covalent bond, those used to immobilize proteins and nucleic acids onto a solid phase through a covalent bond, which are known per se, can be used, and as these examples, amino group, hydroxyl group, sulfhydryl group, isocyanate group, thioisocyanate group, and the like or atomic groups comprising these groups can be mentioned. When a DNA on which amino acids are supported is provided, as a support in the replacing reaction mentioned below, for example, $N^6$-(6-aminohexyl)dATP can be used as a part of dNTP.

Among the above-mentioned binding partners, as those preferred to used as labels in the target DNA, a sort of biotin which will not exert adverse effects on homologous recombination described later in detail, and atomic groups having isocyanate or thioisocyanate group ($C_{1-16}$ alkylene chain which may be interrupted by an oxygen atom) as the functional group when considering availability of a solid support on which surface for example amino acids are supported can be mentioned.

The shape of a solid support may be for example any of plate, microwell, bead, stick and the like as long as it does not exert adverse effects on the bond formation between the members of the binding partner, but the surface characteristics thereof is preferred to be non-porous in general. Another member of the binding partner can be supported onto such a surface. The supporting method per se is known by those skilled in the art. The material of such solid support (which is referred as to solid phase hereinafter) may be any of glass, silicone, natural or synthetic resin. Moreover, the solid support may be a magnetic subject or be processed into a shape of an electrode for its handling convenience.

Labels and labeling method available to label said dNTP with a sort of biotin or an atomic group having other functional group is well known in the art, and some commercially available dNTP (such as biotin-11-dCTP) can be used as they are or a new labeled dNTP may be prepared according to a purpose.

Thus obtained labeled double-stranded DNAs can be immobilized onto a solid surface through a method where the label (a member of the binding partner) born by these double-stranded DNAs and a solid support such as the one mentioned above having another member are incubated in an appropriate aqueous solution which is known per se. Such double-stranded DNAs immobilized onto the solid phase after denatured under a traditional DNA denaturation condition followed by washing off freed single-stranded DNAs can be a so-called DNA array or DNA tip where only a target DNA is immobilized onto the solid phase.

A solid support where the target DNA is immobilized according to the invention can result in a new structure where the target DNA is immobilized at multiple places. Accordingly, a DNA tip having such a structure is provided according to the invention. More specifically, as such DNA tips, those made by the immobilization method of target DNA according to the invention above can be mentioned.

Moreover, the resulting labeled double-stranded DNA will not bind to a solid support, and after denatured under a traditional DNA denaturing condition, the labeled single-stranded DNA molecules and the non-labeled single-stranded DNA molecules are separated. The mixture of those or the labeled single-stranded DNA molecules isolated if needed are used as target DNA in the immobilization method according to the invention or widely used as for example probes of Southern hybridization method or used directly for gene cloning.

In addition, because the preparation method of labeled double-stranded DNA molecules according to the invention can select DNA molecules which are especially double-stranded DNA molecules and the nucleotide sequence of the 3' terminal region or the non-terminal region of the plus strand is homologous to that of the deoxyoligonucleotide added for triple-stranded DNA formation, and can replace said nucleotide sequence with a new nucleotide sequence comprising the labeled nucleotides, using said labels as an indicator, the existence of a certain DNA can be directly detected.

The invention is further illustrated by the following Examples, but it should be understood that these Examples are aimed at facilitating to understand the invention and the invention is not limited to these Examples.

EXAMPLE 1

(A) Triple-strand Formation Using an Deoxyoligonucleotide at the Terminal of a Double-stranded DNA As a double-stranded DNA used as a target, DNA of pBR 322 which nucleotide sequence at the 3' terminal is known [as for the basic sequence, for example, see, Sutcliffe, J. G., Complete nucleotide sequence, of the *Escherichia coli* plasmid pBR322 JOURNAL, Cold Spring Harb. Symp. Duant. Biol. 43Pt1, 77–90 (1979)], which was digested with restriction enzyme Sca I to make it straight (a fragment) was prepared. On the other hand, deoxyoligonucleotide (which is sometimes referred as to "oligo") 1 having the sequence homologous to that of the 3' terminus of the pBR322 Sca I fragment:

| | |
|---|---|
| oligo 1 | 5'-cact gcataattct cttactgtca tgccatccgt aagatgcttt tctgtgactg gtgagt-3' (SEQ ID NO: 1) | and its reverse complementary strand:

| | |
|---|---|
| oligo 2 | 5'-actcac cagtcacaga aaagcatctt acggatggca tgacagtaag agaattatgc agtg-3' (SEQ ID NO: 2) | were synthesized, and these deoxyoligonucleotides were labeled with [γ-$^{32}$P]ATP using commercially available DNA 5' terminal labeling agent (DNA 5' terminal labeling kit MEGALABEL™, Takara Shuzo Co., Ltd.).

For triple-strand formation reaction, two Reaction solutions A (20 μl) and B (20 μl) were prepared. Reaction solution A contains 5 pmol deoxyoligonucleotide 1 (oligo 1), 3.0 μg recA protein, 0.48 mM ATP-γS, 30 mM Tris-acetate (pH 7.2) and 2.5 mM magnesium acetate, whereas Reaction solution B contains 100 ng target DNA, 0.48 mM ATP-γS, 30 mM Tris-acetate (pH 7.2) and 2.15 mM magnesium acetate. Reaction solutions A and B were incubated individually at 37° C. for from 30 min to 18 hr. Then, in order to remove proteins, to the whole amount of the triple-strand formation reaction solution, 0.5% (w/vol) SDS, 0.7 mg/ml Proteinase K were added and incubated at 37° C. for 10 min. Ten μl thereof was electrophorased in 0.8% agarose gel. After the electrophoresis, the gel was stained with ethidium bromide and photographs of the gel were taken to observe the DNA.

Figure 2A:
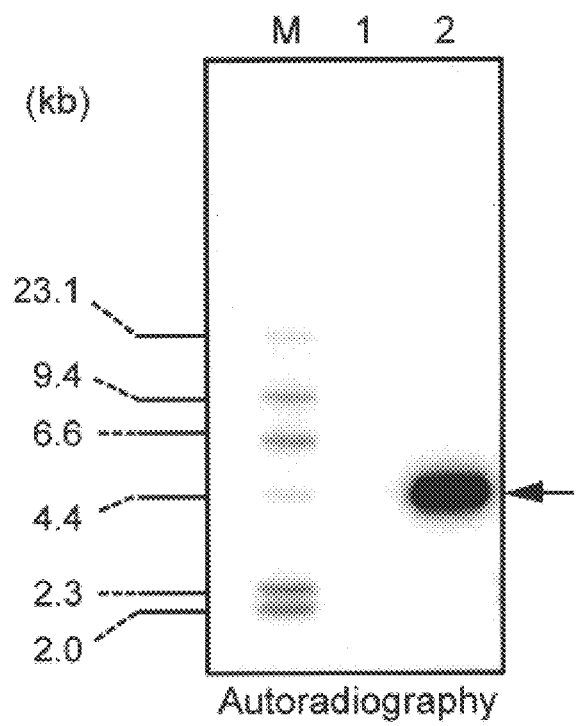
FIG. 2 is an autoradiograph (A) and photograph (B) showing electrophoretical behavior on a gel submitted to autoradiography and gel stained with ethidium bromide after agarose-gel electrophoresis conducted in Example 1(A).
Figure 2B:
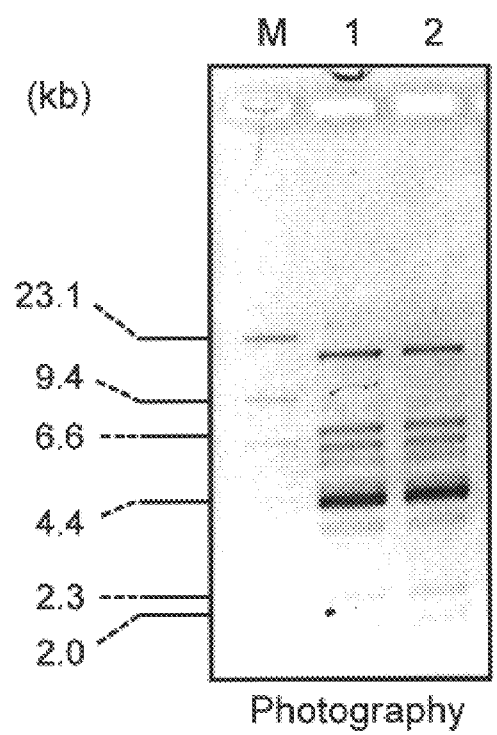

The result is shown in FIG. 2 (autoradiograph (A) and photograph (B)). Lane M-2 in FIG. 2 show the following meanings or outcomes.

Lane M: DNA size markers

Lane 1: The sample is from the reaction conducted using oligo 2. In order to investigate basic sequence specificity, λDNA fragment digested with restriction enzyme BstP I was also included in the reaction. With the sequence of oligo 2, no triple-strand is formed.

Lane 2: The sample is from the reaction conducted using oligo 1. In order to investigate basic sequence specificity, λDNA fragment digested with restriction enzyme BstP I was also included in the reaction. Triple-strand can be formed with oligo 1.

Here, the DNA size marker in Lane M is λDNA digested with restriction enzyme HindIII and labeled with [γ-$^{32}$P] ATP.

In a series of the reactions in this experiment, among hose to form triple-stranded DNAs using two 60-mer deoxyoligonucleotides, one has the sequence at the 3' terminal region of the plus strand in the double-strand DNA molecule (shown in Lane 2). Another one has the sequence at the 5' terminal region of the minus strand in the double-stranded DNA molecule (shown in Lane 1).

(B-1) Substitution of the Nucleotide Sequence at the 3' Terminal Region of the Plus Strand in the Double-stranded DNA To the above Proteinase K-treated solution (40 μl), 60 μl of TE solution (10 mM Tris-HCl, 1 mM EDTA) was added to 100 μl. After one time of phenol/chloroform extraction and one time of chloroform extraction, ethanol was added and the mixture was subjected to cooled centrifugation to separate and concentrate the contained DNA molecule. After dissolving the DNA precipitate in 10.5 μl distilled water, it was kept warm at 37° C. for 15 min in 10 mM Tris-HCl pH 7.5, 5 mM MgCl$_2$, 7.5 mM dithiothreitol, 4 units of Klenow enzyme, 0.02 mM [α-$^{32}$P]dATP, 0.02 mM cDTP, 0.02 mM dATP and 0.02 mM dTTP. Ten μl of TE buffering solution was added and excessive [α-$^{32}$P]dATP was removed using G25 spin column. The 10 μl solution was electrophoresed in 0.8% agarose gel. After the electrophoresis, the gel was stained with ethidium bromide, photographs of the gel were taken as the record, and then the gel was dried on a paper filter in a gel drier. For signal detection, autoradiogram of the dried gel was taken, which was recorded on a X-ray film.

Figure 3A:
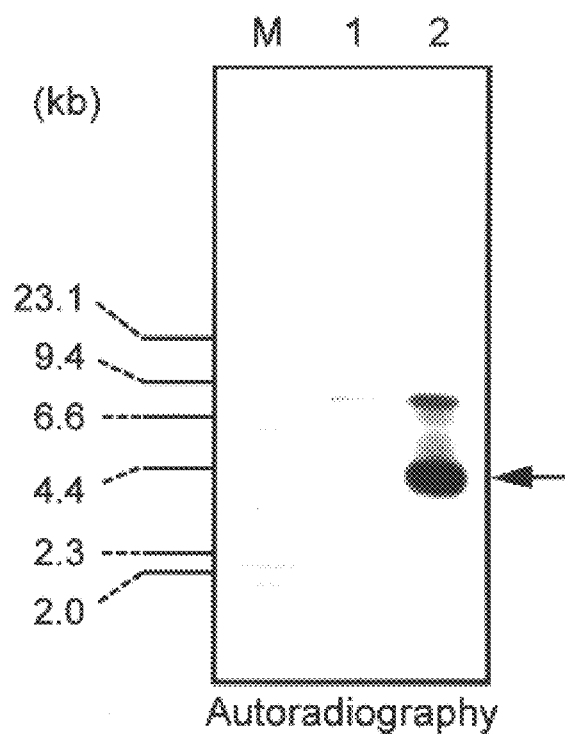
FIG. 3 is an autoradiograph (A) showing electrophoretical behavior on a gel submitted to autoradiography and a gel stained with ethidium bromide after agarose-gel electrophoresis conducted in Example 1(B).
Figure 3B:
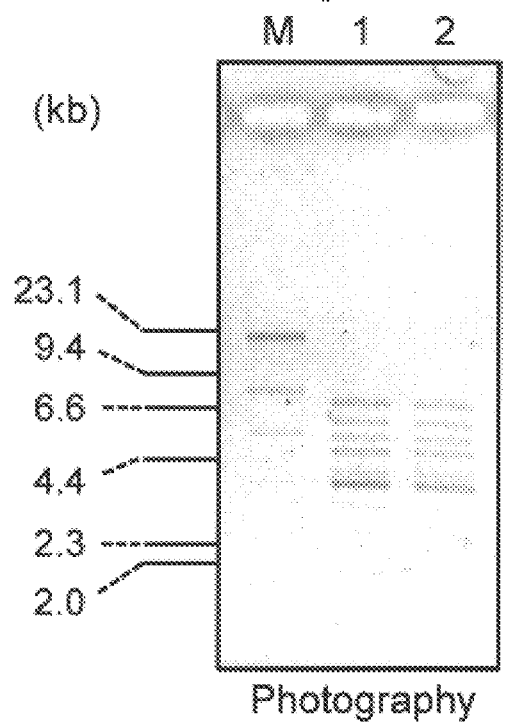

The result was shown in FIG. 3 (autoradiograph (A) and photograph (B)). Lane M-2 shown in the photographs show the following meanings or results, respectively.

Lane M: DNA size maker.

Lane 1: The result is shown from [α-$^{32}$P]dATP incorporation label reaction without using the 60 base deoxyoligonucleotide. In order to search basic sequence specificity, λDNA digested with restriction enzyme Bst I was also included in this reaction at the same time.

Lane 2: The result is shown from the reaction using a 60 base deoxyoligonucleotide having the sequence at the 3' terminal region of the plus strand in the target double-stranded DNA molecule, followed by [α-$^{32}$P]dATP incorporation labeling reaction. In order to investigate basic sequence specificity, λDNA digested with restriction enzyme BstP I was also included in this reaction at the same time.

Here, the size markers in Lane 1 is λDNA digested with restriction enzyme HindIII and labeled with [γ-$^{32}$P]ATP.

In a series of reactions in this experiment, at triple-stranded formation before incorporation reaction of $^{32}$P into the target double-stranded DNA molecule by Klenow enzyme, the outcomes from the reaction conducted with an deoxyoligonucleotide having the sequence of the plus strand (the result is shown in Lane 2) and from the reaction conducted without any deoxyoligonucleotide (the result is shown in Lane 1). From these results, it is shown that triple-strand formation is essential for labeling the target double-stranded DNA molecule. Moreover, from the fact that λDNA used also in the same reaction is not labeled, it is shown that the way to label is specific to the basic sequence of DNA.

Lane 2: The result was shown from the reaction using the 60 base deoxyoligonucleotide having the sequence at the 3' terminal region of the plus strand in the target double-stranded DNA molecule followed by [α-$^{32}$P]dATP incorporation labeling reaction. In order to investigate basic sequence specificity, λDNA digested with restriction enzyme BstP I was also included in this reaction at the same time.

Figure 4:
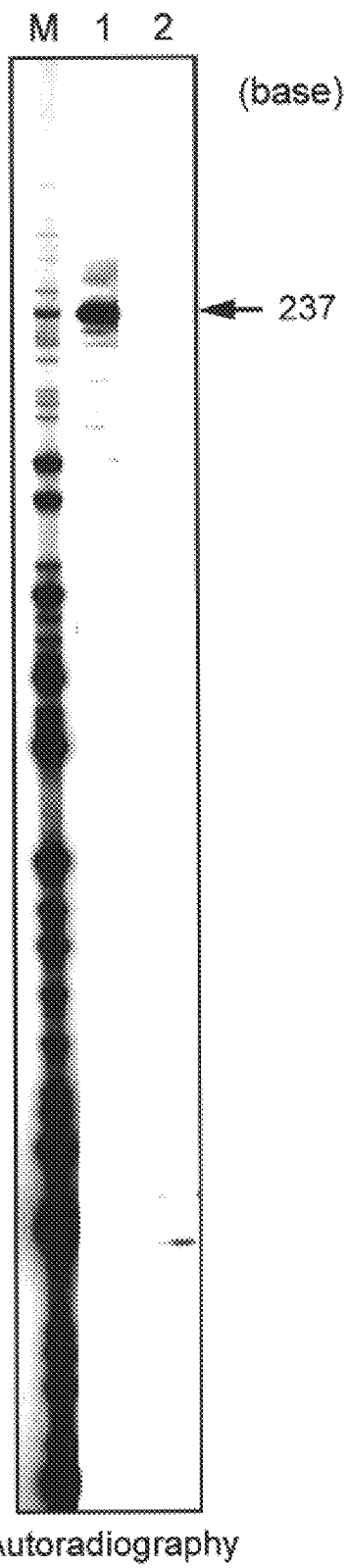
FIG. 4 is an autoradiograph showing electrophoretical behavior on a gel submitted to autoradiography after electrophoresed in a denatured polyacrylamide gel (which is commonly called as sequencing gel) conducted in Example 1(B-2).

(B-2) Identification of the Length of DNA Strand where a Double-stranded DNA Labeling Material was Incorporated The reaction product of (B-1) was digested with restriction enzyme Pst I, and the resulting single-stranded DNA was analyzed as it was after it was electrophorased in a denatured polyacrylamide gel. The result were shown in FIG. 4 (photographs). Lane M-2 in the autoradiographs show the following meanings and results, respectively.

Lane M: DNA size maker.

Lane 1: The result is shown from [α-$^{32}$P]dATP incorporation label reaction using the 60 base deoxyoligonucleotide having the sequence of the 3' terminal region of the plus strand in the target double-stranded DNA molecule. In order to search basic sequence specificity, λDNA digested with restriction enzyme BstP I was also included in this reaction at the same time.

Lane 2: The result is shown from [α-$^{32}$P]dATP incorporation label reaction without using the 60 base deoxyoligonucleotide. In order to search basic sequence specificity, λDNA digested with restriction enzyme BstP I was also included in this reaction at the same time.

Here, Lane M is size markers of single-stranded DNA molecules.

In a series of reactions in this example, at triple-stranded formation before incorporation reaction of $^{32}$P into the target double-stranded DNA molecule by Klenow enzyme, double-stranded DNAs are electrophorased after denatured into single-strands when analyzed in a denatured polyacrylamide gel as the outcomes from the reaction conducted using the deoxyoligonucleotide having the sequence of the plus strand (the result is shown in Lane 1) and from the reaction conducted without using deoxyoligonucleotides (the result is shown in Lane 2). Because the target DNA immediately before electrophoresis has been a straight target DNA further digested with restriction enzyme Pst I, the length of the plus strand is 237 base and of the minus strand is 241 base. It is shown from the information of the size makers in Lane M that the length of the signal in Lane 1 is 237 base. From these results, it is shown that the labeled DNA is the plus strand in the double-stranded DNA.

EXAMPLE 2

Dependency of the Individual Reaction Components in the Labeling Reaction

Phage vector M13 mp18 RF DNA (available from Takara Shuzo Co., Ltd.) made straight with restriction enzyme SnaB I as the target DNA and 60-mer deoxyoligonucleotide 3 (oligo 3) having the sequence at the terminal region of the target DNA were prepared. In order to conduct triple-strand formation reaction between the target DNA and deoxyoligonucleotide 3 (oligo 3), two Reaction solutions A (20 µl) and B (20 µl) were prepared. Reaction solution A contains 5 pmol deoxyoligonucleotide 1 (oligol), 6.0 µg recA protein, 0.48 mM ATP-γS, 30 mM Tris-acetate (pH 7.2) and 2.5 mM magnesium acetate. Reaction solution B contains 200 ng target DNA, 0.48 mM ATP-γS, 30 mM Tris-acetate (pH 7.2) and 2.15 mM magnesium acetate.

After incubating Reaction solutions A and B individually at 37° C. for 15 min, the two were mixed and further incubated at 37° C. for 30 min. To 40 µl of the reaction solution after triple-strand formation, 0.5% (w/v) SDS, 0.7 mg/ml Proteinase K were added and incubated at 37° C. for 10 min to conduct recA removal treatment. After then, 60 µl of TE buffering solution (10 mM Tris-HCl, 1 mM EDTA) was added, and one time of phenol/chloroform extraction followed by ethanol precipitation was conducted to concentrate and separate the included DNA molecules. After the DNA precipitate was dissolved into 10.5 µl of distilled water, it was incubated at 37° C. for 15 min in 10 mM Tris-HCl pH 7.5, 5 mM MgCl$_2$, 7.5 mM dithiothreitol, 4 units of Klenow fragment, 0.02 mM [α-$^{32}$P]dCTP, 0.02 mM cDTP, 0.02 mM dATP and 0.02 mM dTTP to conduct the labeling reaction.

After 10 µl of TE buffering solution was added and excessive [α-$^{32}$P]dCTP was removed using G25 spin column, the half amount thereof was electrophoeased in 1% agarose gel, and the remaining half in 0.7% alkaline denaturing gel. For agarose gel electrophoresis, after the run, the gel was stained with ethidium bromide, photographs of the gel were taken as the record. The result is shown in Lane 1 in FIG. 5(B). After then, the gel was dried on a paper filter in a gel drier. For signal detection, autoradiogram of the dried gel was taken, which was recorded on a X-ray film. The results of agarose gel electrophoresis and alkaline gel electrophoresis are shown in Lane 1 in FIG. 5(A) and Lane 1 in FIG. 5(C), respectively.

As a comparative experiments, the followings were conducted. Lane M contains DNA size makers and the sizes are shown at the left side of the diagram. The size markers were λDNA digested with restriction enzyme HindIII and labeled with [γ-$^{32}$P]ATP at the 5' termini. Lane 2 shows the result from the same reaction as Lane 1 except for conducting the reaction without addition of recA. Lane 3 shows the result from the same reaction as Lane 1 except for conducting the reaction without addition of ATP-γS. Lane 4 shows the result from the same reaction as Lane 1 except for conducting the reaction using deoxyoligonucleotide 4 (oligo 4) having the reverse complementary sequence. Lane 5 shows the result from the same reaction as Lane 1 except for conducting the reaction using deoxyoligonucleotide 1 (oligo 1) having pBR322 DNA sequence.

The sequence of oligo 3:

5'-agaggctttg aggactaaag actttttcat gaggaagttt ccattaaacg ggtaaaatac-3'        (SEQ ID NO: 3)

The sequence of oligo 4:

5'-gtattttacc cgtttaatgg aaacttcctc atgaaaaagt ctttagtcct caaagcctct-3'        (SEQ ID NO: 4)

The sequence of oligo 1:

5'-cact gcataattct cttactgtca tgccatccgt aagatgcttt tctgtgactg gtgagt-3'        (SEQ ID NO: 1)

Figure 5A:
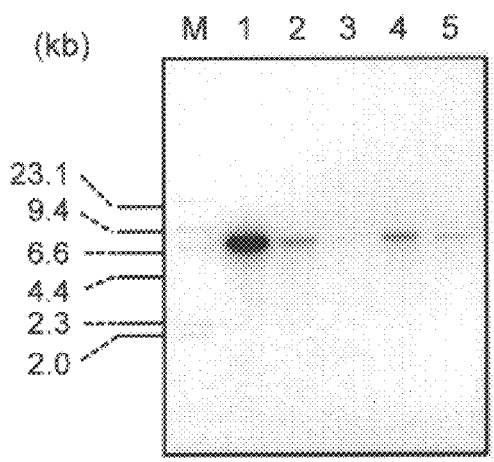
FIGS. 5A, B and C are autoradiographs (A and C) and a photograph (B) showing electrophoretical behavior on a gel submitted to autoradiography or stained with ethidium bromide after agarose gel electrophoresis, as conducted in Example 2.
Figure 5C:
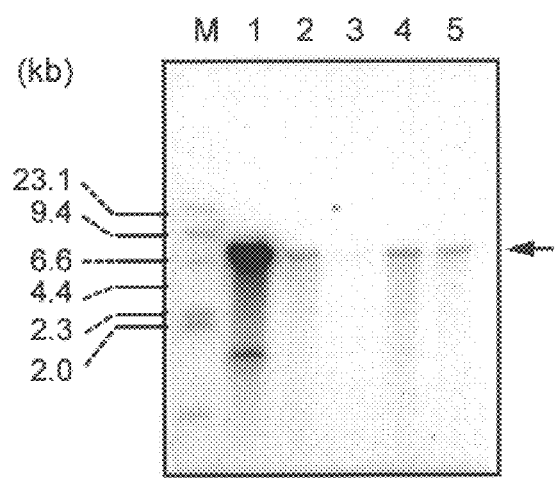
Figure 5B:
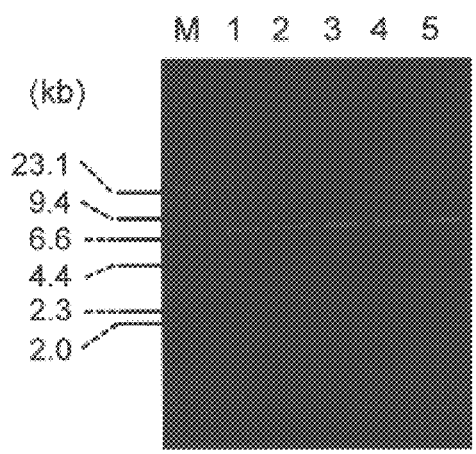

According to FIGS. 5(A), (B) and (C), as shown in Lane 1 in FIG. 5(A), a various treatment conditions bearing the outcome of Lane 1 is proven to be essential for labeling reaction of target DNAs. Moreover, as shown in Lane 1 of FIG. 5(C), where the label is incorporated is the target DNA and it is proven that the length of the label-incorporated target DNA is the same as that of the target DNA before the label incorporation.

EXAMPLE 3

Strand Length of Labeled Target DNAs

Figure 6A:
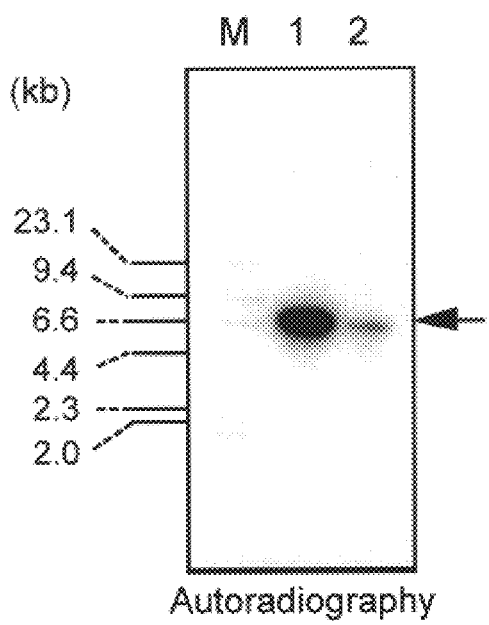
FIGS. 6A, B and C are autoradiographs (A and C) and a photograph (B) showing electrophoretical behavior on a gel submitted to autoradiography or stained with ethidium bromide after agarose gel electrophoresis, as conducted in Example 3.
Figure 6B:
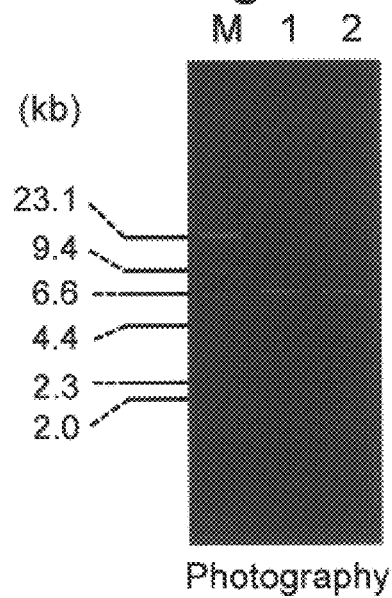
Figure 6C:
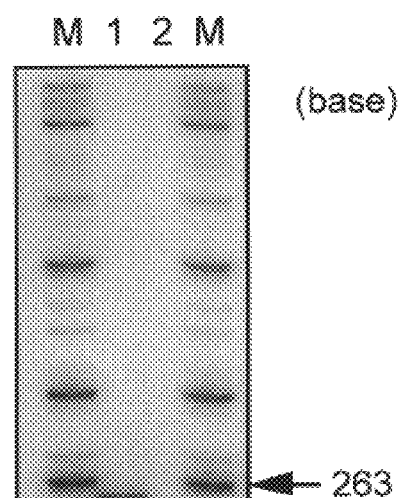

Lane 1 of FIG. 6(A) shows the result from the same reaction as in Lane 1 of FIG. 5(A) except for using M13 mp18 RF DNA digested with restriction enzyme Hinc II as the target DNA and using deoxyoligonucleotide 5 (oligo 5) having the sequence at the terminal region. As a comparative experiment, Lane 2 shows the result from the same reaction as in Lane 1 without addition of the deoxyoligonucleotide. FIG. 6(B) is a photograph of the gel stained. Lane 1 of FIG. 6(C) contains the sample obtained in Lane 1 of (A) digested with restriction enzyme BsaH I and electrophorased in a 4.5% denatured polyacrylamide gel. Lane 2 contains the sample obtained in Lane 2 of (A) digested with restriction enzyme BsaH I and electrophorased in the same way as in Lane 1. Lane M is DNA size markers and one of the sizes is shown at the left side of (C).

The sequence of oligo 5:

5'-ggaaacagct atgaccatga ttacgaattc gagctcggta cccggggatc
ctctagagtc-3'                                  (SEQ ID NO: 5)

According to FIGS. 6(A), (B) and (C), as shown in Lane 1 of (C), it is proven that the labeled DNA is one of the single-strand of the target double-stranded DNA and its whole length is 263 bp.

EXAMPLE 4

Basic Sequence Specificity in the Labeling Reaction

Figure 7A:
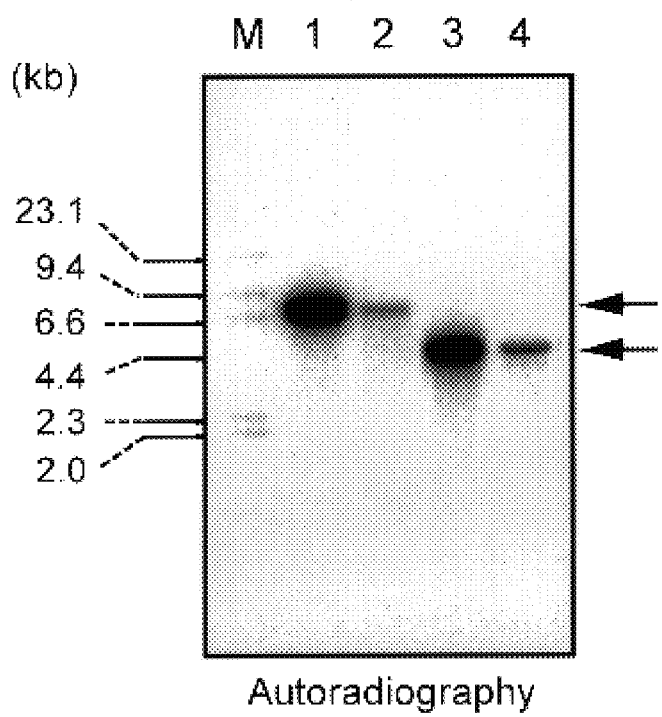
FIG. 7 is an autoradiograph (A) and a photograph (B) showing electrophoretical behavior on a gel submitted to autoradiography or stained with ethidium bromide after agarose gel electrophoresis, as conducted in Example 4.
Figure 7B:
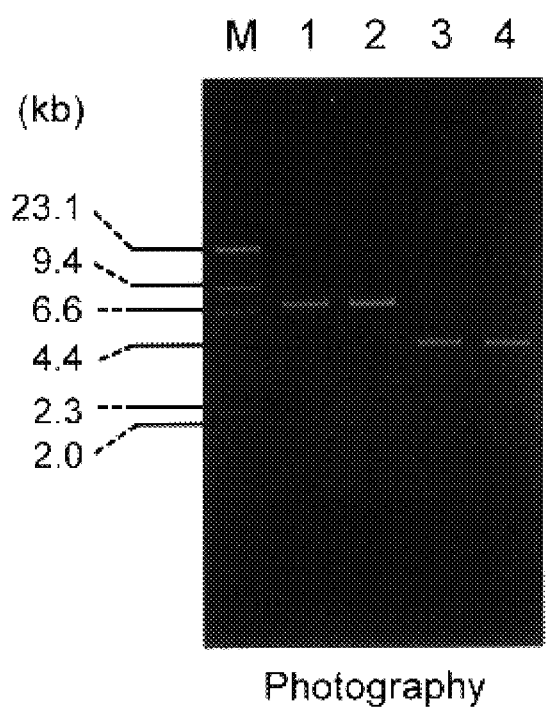

Lane 1 of FIG. 7(A) shows the result from the same reaction as Lane 1 of FIG. 5(A). Lane 2 shows the result from the same reaction as Lane 1 except for using deoxyoligonucleotide 1 (oligo 1) above having the sequence of pBR322 DNA (available from Takara Shuzo Co., Ltd.). Lane 3 shows the result from the same reaction as Lane 1 except for using pBR322 DNA digested with restriction enzyme Sca I as the target DNA and using deoxyoligonucleotide 1 (oligo 1) having the sequence at the terminal region. Lane 4 shows the result from the same reaction as Lane 1 except for using pBR322 DNA digested with restriction enzyme Sca I as the target DNA and using deoxyoligonucleotide 3 (oligo 3) having the sequence of M13 mp18 RF DNA. (B) is the whole picture of the stained DNA on the same agarose gel as (A).

According to FIGS. 7(A) and (B), the labeling reaction shows that it is essential that the deoxyoligonucleotide sequence at the terminal region of the target DNA and that used in the labeling reaction are substantially homologous.

EXAMPLE 5

Labeled Location of the Target DNA in the Labeling Reaction

Figure 8A:
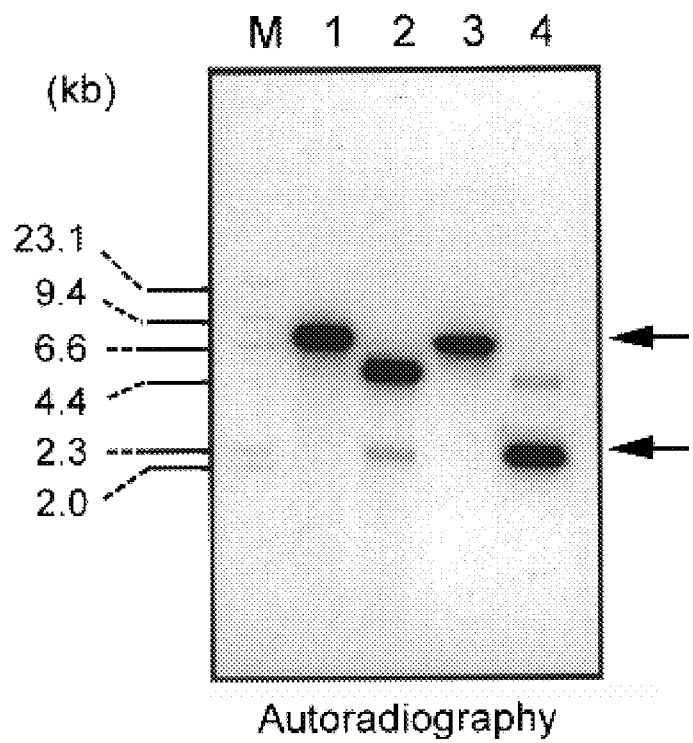
FIG. 8 is an autoradiograph (A) and a photograph (B) showing electrophoretical behavior on a gel submitted to autoradiography or stained with ethidium bromide after agarose gel electrophoresis, as conducted in Example 5. Lane M: molecular markers (kb). Lane 1: M13 mp18 RF DNA digested with SnaB I and a deoxyoligonucleotide having the sequence of the terminal region of the target DNA. Lane 2: same reaction as Lane 1, but the DNA is digested with EcoR I. Lane 3: contains a sample from the reaction conducted using the target DNA obtained by digesting M13 mp18RF DNA with restriction enzyme SnaB I and a deoxyoligonucleotide having the sequence of another terminal region of M13 mp18 RF DNA digested with SnaB I (oligo 6). Lane 4: same reaction as Lane 3, but the DNA is digested with EcoR I.
Figure 8B:
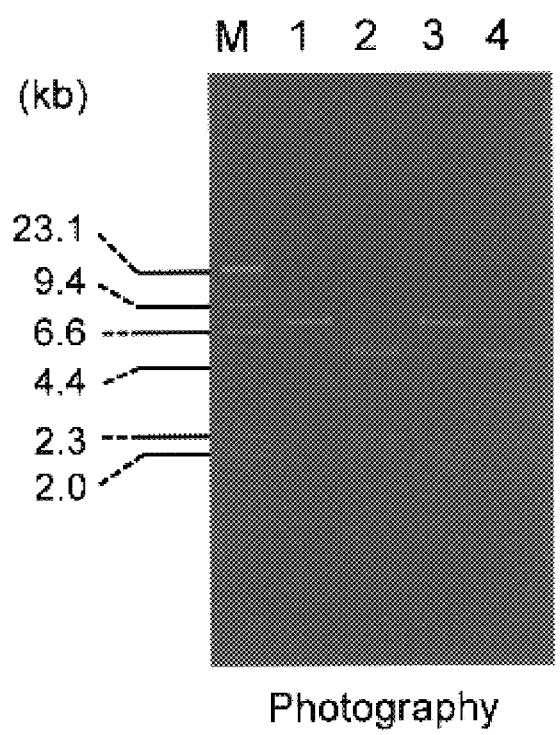

Lane 1 of FIG. 8(A) show the result from the same reaction as Lane 1 of FIG. 5(A). Lane 2 contains the sample from electrophoresis of the same sample as Lane 1 which corresponds to the nucleotide sequence at another terminal sides of the phage vector M13 mp18 RF SnaB I fragment which is further digested with restriction enzyme EcoR I. Lane 4 contains the sample electrophorased after digested with restriction enzyme EcoR I. (B) is the whole picture of the same stained agarose gel as (A).

The sequence of oligo 6:

5'-tgttttagtg tattctttcg cctctttcgt tttaggttgg tgccttcgta
gtggcattac-3'                                  (SEQ ID NO: 6)

According to FIGS. 8(A) and (B), as shown in Lane 2 and Lane 4, when a series of reactions are conducted using two types deoxyoligonucleotides 3 (oligo 3) and 6 (oligo 6) having the sequences at each terminal region of the target DNA, respectively, it is proven that the terminal regions where the individual deoxyoligonucleotides form triple-strands are labeled at the termini.

EXAMPLE 6

Labeled Location of the Target DNA in the Labeling Reaction

Figure 9A:
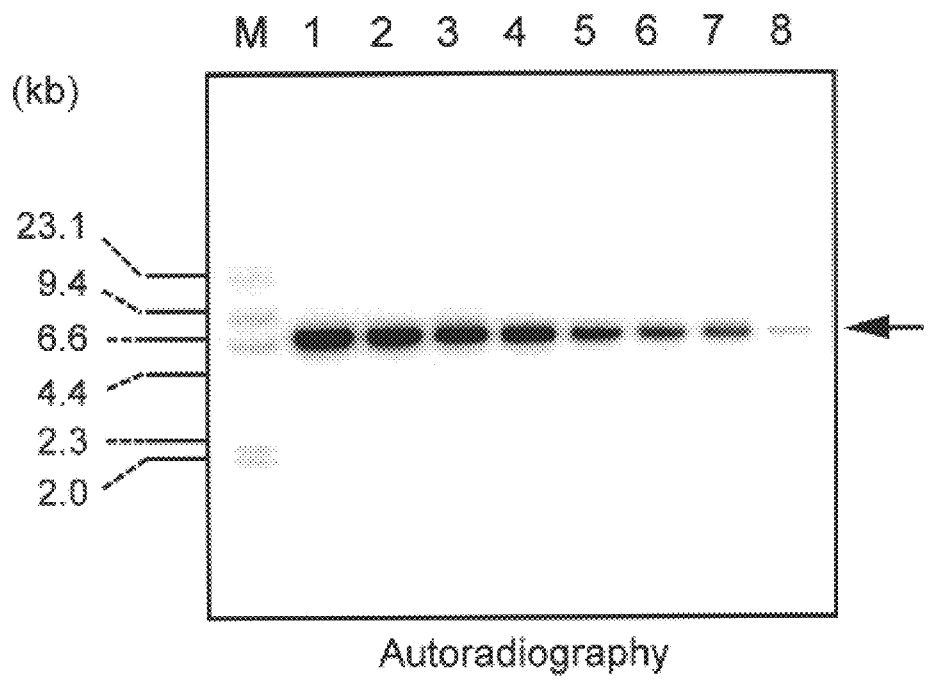
FIG. 9 is an autoradiograph (A) and a photograph (B) showing electrophoretical behavior on a gel submitted to autoradiography or stained with ethidium bromide after agarose gel electrophoresis, as conducted in Example 6. Lane M: molecular markers (kb). Lane 1: M13 mp18 RF DNA digested with Hinc II and a deoxyoligonucleotide having the sequence of the terminal region of the target DNA. Lane 2: same reaction as Lane 1, but the DNA is digested with Xba I. Lane 3: same reaction as Lane 1, but the DNA is digested with BamH I. Lane 4: same reaction as Lane 1, but the DNA is digested with Sma I. Lane 5: same reaction as Lane 1, but the DNA is digested with Kpn I. Lane 6: Same reaction as Lane 1, but the DNA is digested with Sac I. Lane 7: same reaction as Lane 1, but the DNA is digested with EcoR I. Lane 8: same reaction as Lane 1, but the DNA is digested with BsaH I.
Figure 9B:
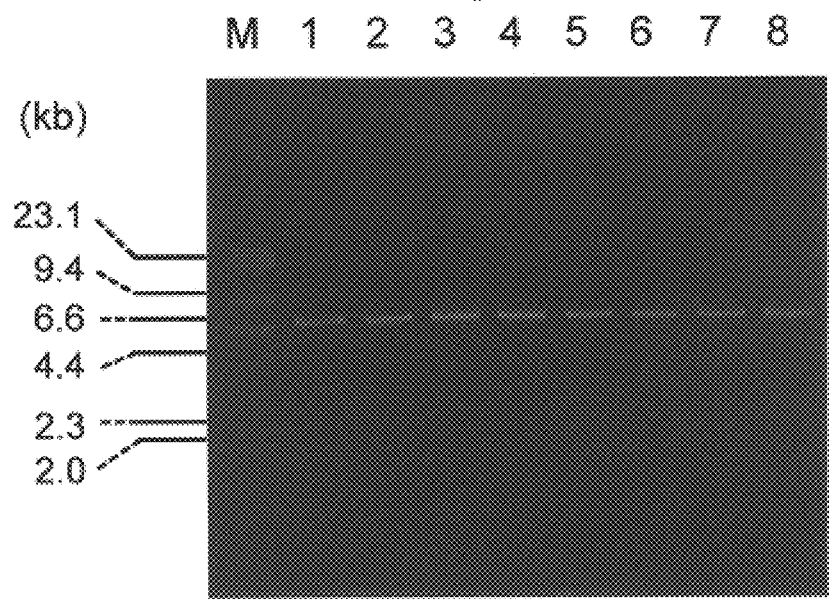

Lane 1 of the FIG. 9(A) shows the result from the same reaction as Lane 1 of FIG. 5(A) except for using M13 mp18 RF DNA digested with restriction enzyme Hinc II as the target DNA and using deoxyoligonucleotide 7 (oligo 7) having the sequence at the terminal region. Lane 2 shows the result from the same sample as Lane 1 digested with restriction enzyme Xba I and electrophorased. Lane 4 shows the result from the same sample digested with restriction enzyme Sma I. Lane 5 shows the result from the same sample digested with restriction enzyme Kpn I. Lane 6 shows the result from the same sample digested with restriction enzyme Sac I. Lane 7 shows the result from the same sample digested with restriction enzyme EcoR I. Lane 8 shows the result from the same sample digested with restriction enzyme Bsa II. (B) is the whole picture of the same stained agarose gel as (A).

The sequence of oligo 7:

5'-ttacgaattc gagctcggta cccggggatc
ctctagagtc-3'                                  (SEQ ID NO: 7)

According to FIGS. 9(A) and (B), as shown in Lane 1 and Lane 2, because when the region where the labels in the target DNA have been incorporated is cut with the restriction enzyme in tern from the terminus, it is proven that as the number of the labels decreases correspondingly, the labeled region in the target DNA is the terminal region of the DNA. And also proven is that the labeled region is included within the length of the deoxyoligonucleotide and is uniformly labeled.

EXAMPLE 7

The labeling reaction using different DNA polymerases

Figure 10A:
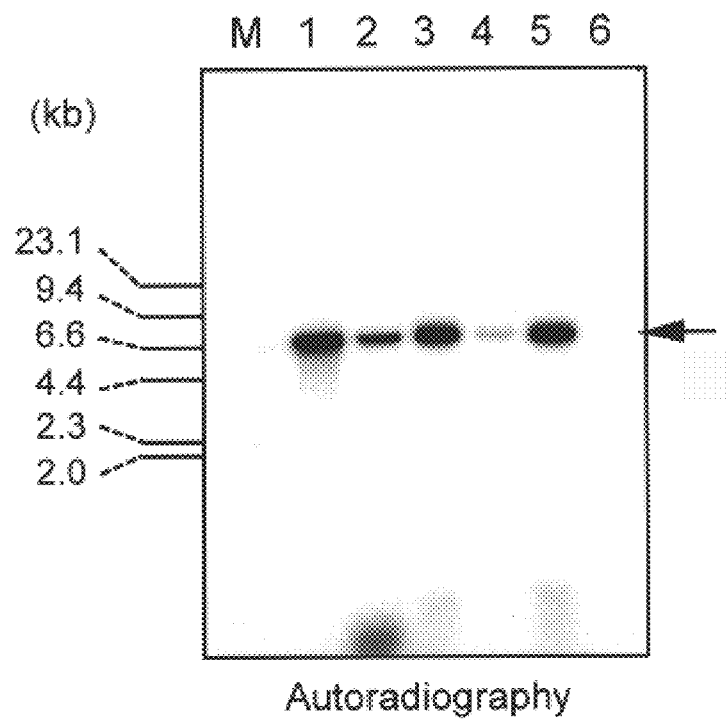
FIG. 10 is an autoradiograph (A) and a photograph (B) showing electrophoretical behavior on a gel submitted to autoradiography or stained with ethidium bromide after agarose gel electrophoresis, as conducted in Example 7.
Figure 10B:
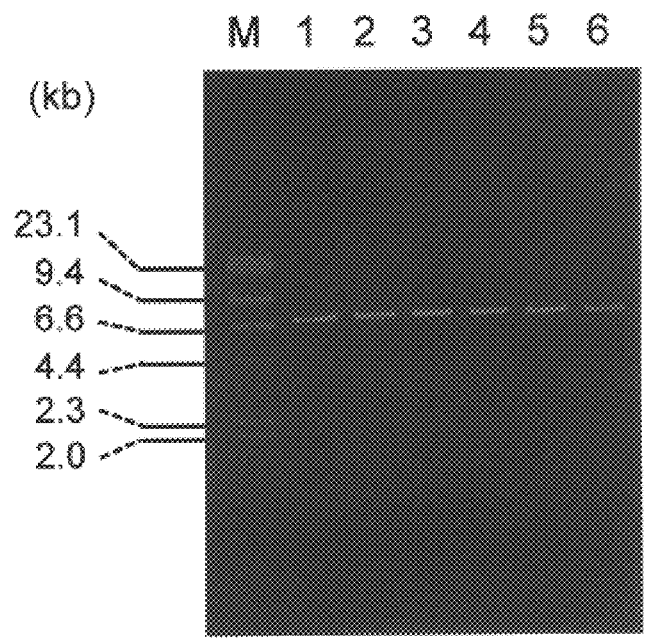

Lane 1 of FIG. 10(A) shows the result from the same reaction as Lane 1 of FIG. 5(A) except for using E. coli DNA Polymerase I in the labeling reaction. Lane 2 shows the result from the same reaction as Lane 1 of FIG. 5(A) except for conducting the reaction without addition of the deoxyoligonucleotide. Lane 3 shows the result from the same reaction as Lane 1 of FIG. 5(A) except for conducting the labeling reaction with E. coli DNA Polymerase I, Large fragment. Lane 4 shows the result from the same reaction as Lane 1 of FIG. 5(A) except for conducting the labeling reaction with E. coli DNA Polymerase I, Large fragment and conducting the reaction without addition of the deoxyoligonucleotide. Lane 5 shows the result from the same reaction as Lane 1 of FIG. 5(A). Lane 6 shows the result from the same reaction as Lane 1 of FIG. 5(A) except for conducting the reaction without addition of the deoxyoligonucleotide.

According to FIGS. 10(A) and (B), it is proven that any type of DNA Polymerase I enzymes can be used in the labeling reaction. Moreover, as shown in Lane 6, to reduce the background, it is proven that the labeling reaction is preferably conducted with E. coli DNA Polymerase I, Large fragment (3'→5' exo minus).

EXAMPLE 8

The Labeling Reaction Using Different Types of DNA Polymerases

Figure 11A:
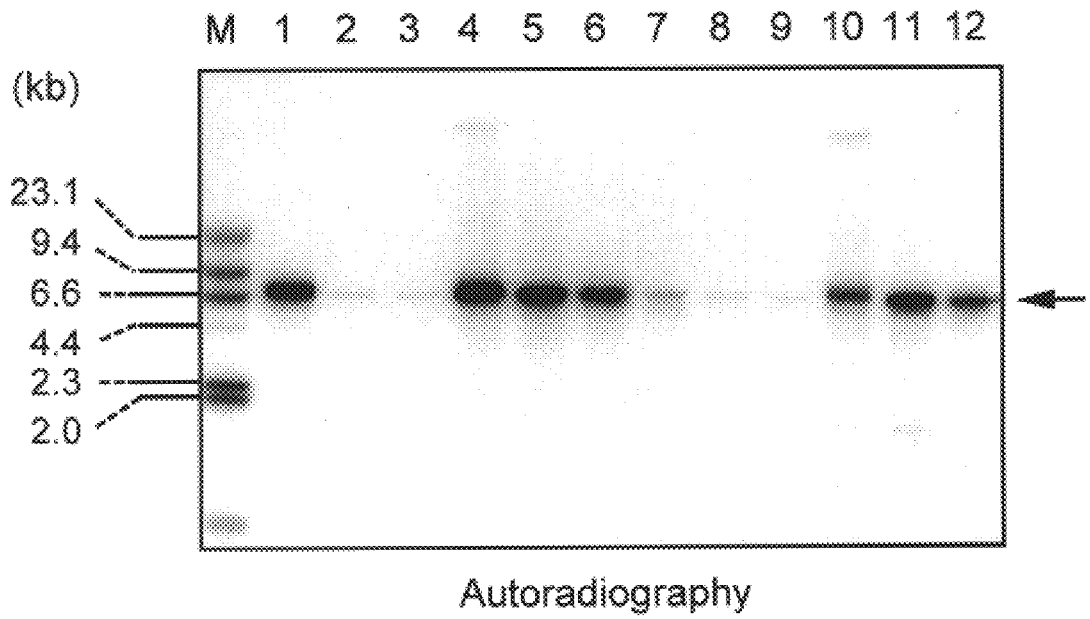
FIG. 11 is an autoradiograph (A) and a photograph (B) showing electrophoretical behavior on a gel submitted to autoradiography or stained with ethidium bromide after agarose gel electrophoresis, as conducted in Example 8.
Figure 11B:
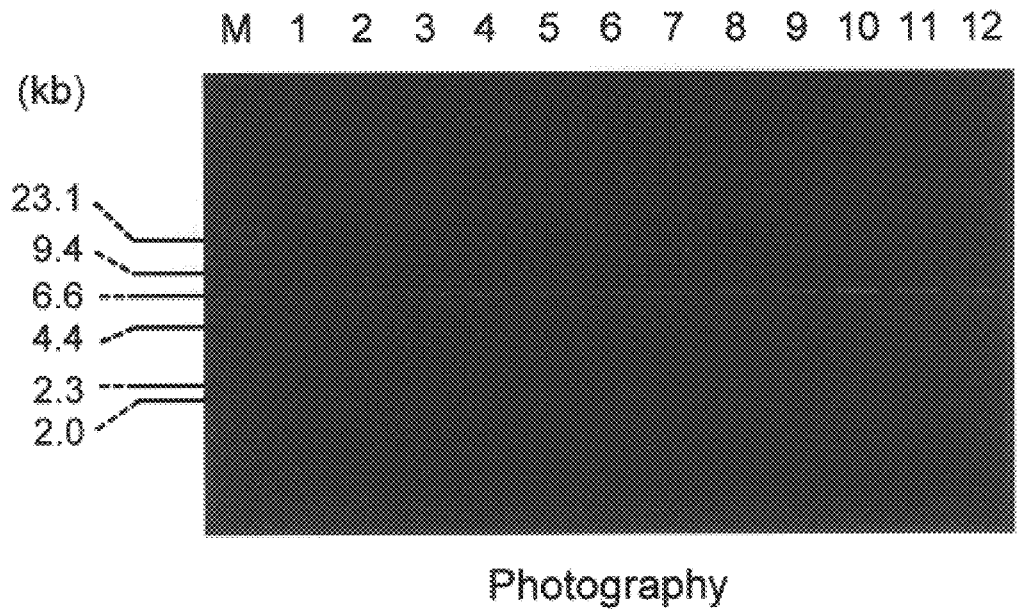

Lane 1 of FIG. 11(A) shows the result from the same reaction as Lane 1 of FIG. 5(A). Lane 7 shows the result from the same reaction as Lane 1 of FIG. 5(A) except for conducting the reaction without addition of the deoxyoligonucleotide. Lane 2 shows the result from the triple-strand formation between M13 mp18 RF DNA digested with restriction enzyme SnaB I to make it straight as the target DNA and deoxyoligonucleotide 1 (oligo 1). For the reaction, two Reaction solutions A (20 µl) and B (20 µl) were prepared. Reaction solution A contains 5 pmol deoxyoligonucleotide 1 (oligo 1), 6.0 µg recA protein, 0.48 mM ATP-γS, 30 mM Tris-acetate (pH 7.2) and 2.5 mM magnesium acetate. Reaction solution B contains 200 ng target DNA, 0.48 mM ATP-γS, 30 mM Tris-acetate (pH 7.2) and 2.15 mM magnesium acetate.

After incubating Reaction solutions A and B individually at 37° C. for 15 min, the two were mixed and further incubated at 37° C. for 30 min. At this time, the amount of the reaction solution after the recombination reaction was 40 µl. Ten µl thereof was incubated in 20 µl of a reaction solution containing 10 mM Tris-HCl pH 7.5, 5 mM MgCl$_2$, 7.5 mM dithiothreitol, 4 units of Klenow fragment, 0.02 mM γ-$^{32}$P dCTP, 0.02 mM dGTP, 0.02 mM dATP and 0.02 mM dTTP at 37° C. for 60 min. After adding 0.5% (w/v) SDS, 0.7 mg/ml Proteinase K to the whole amount and incubating it at 37° C. for 10 min, 30 µl of TE buffering solution was added and excessive α-$^{32}$P dCTP was removed with G25 spin column. The half amount thereof was electrophorased in an 1% agarose gel. After the run, the gel was stained with ethidium bromide and photographs of the gel were taken for DNA observation. Signal was detected by taking autoradiography of the dried gel and then recorded on a X-ray film.

Lane 8 shows the result from the same reaction as Lane 2 except for conducting the reaction without addition of the deoxyoligonucleotide. Lane 3 shows the result from the same reaction as Lane 2 except for conducting the labeling reaction at 45° C. Lane 9 shows the result from the same reaction as Lane 2 except for conducting the reaction without addition of the deoxyoligonucleotide. Lane 4 shows the result from the same reaction as Lane 2 except for conducting the labeling reaction through incubation in 20 µl of a reaction solution containing 20 mM Tris-HCl pH 8.8, 10 mM KCl, 10 mM (NH$_4$)$_2$SO$_4$, 2 mM MgSO$_4$, 0.1% Triton X-100, 5 units of Bst DNA Polymerase Large fragment, 0.02 mM α-$^{32}$P dCTP, 0.02 mM dGTP, 0.02 mM dATP and 0.02 mM dTTP at 65° C. for 60 min. Lane 10 shows the result from the same reaction as Lane 4 except for conducting the reaction without addition of the deoxyoligonucleotide. Lane 5 shows the result from the same reaction as Lane 2 except for conducting the labeling reaction through incubation in 20 µl of a reaction solution containing 20 mM Tris-HCl pH 8.3, 10 mM KCl, 10 mM KCl, 6 mM (NH$_4$)$_2$SO$_4$, 2 mM MgCl$_2$, 0.1% Triton X-100, 0.001% BSA, 5 units of PyroBest DNA Polymerase Large fragment, 0.02 mM [α-$^{32}$P]dCTP, 0.02 mM dGTP, 0.02 mM dATP and 0.02 mM dTTP at 65° C. for 60 min. Lane 11 shows the result from the same reaction as Lane 5 except for conducting the reaction without addition of the deoxyoligonucleotide. Lane 6 shows the result from the same reaction as Lane 2 except for conducting the labeling reaction through incubation in 20 µl of a reaction solution containing 10 mM Tris-HCl pH 8.3, 50 mM KCl, 1.5 mM MgCl$_2$, 5 units of Taq DNA Polymerase Large fragment, 0.02 mM [α-$^{32}$P]dCTP, 0.02 mM dGTP, 0.02 mM dATP and 0.02 mM dTTP at 65° C. for 60 min. Lane 12 shows the result from the same reaction as Lane 6 except for conducting the reaction without addition of the deoxyoligonucleotide. (B) is the whole picture of the stained DNA on the same agarose gel as (A).

According to FIGS. 11(A) and (B), as shown in Lane 4, by conducting the labeling reaction using thermostable Bst DNA Polymerase, the labeling reaction can be conducted without recA removal treatment. Moreover, by a comparison between Lane 1 and Lane 4, it is proven that the labeling efficiency is almost the same as the case where the labeling reaction is conducted with removal of recA.

EXAMPLE 9

The Labeling Reaction Using a Circular Target DNA

A circular DNA (pBR322 DNA) as the target DNA and deoxyoligonucleotide 8 (oligo 8) of 120-mer having a part of sequence thereof were prepared. In order to conduct triple-strand formation reaction between the target DNA and deoxyoligonucleotide 8 (oligo 8), two Reaction solutions A (20 µl) and B (20 µl) were prepared. Reaction solution A contains 5 pmol deoxyoligonucleotide 8 (oligo 8), 6.0 µg recA protein, 0.48 mM ATP-γS, 30 mM Tris-acetate (H 7.2) and 2.5 mM magnesium acetate. Reaction solution B contains 200 ng target DNA, 0.48 mM ATP-γS, 30 mM Tris-acetate (pH 7.2) and 2.15 mM magnesium acetate.

After incubating Reaction solutions A and B individually at 37° C. for 15 min, the two were mixed and further incubated at 37° C. for 30 min. To 40 µl of the reaction solution at this time after triple-strand formation, 0.5% (w/v) SDS, 0.7 mg/ml Proteinase K were added and incubated at 37° C. for 10 min to conduct recA removal treatment. After then, 60 µl of TE buffering solution (10 mM Tris-HCl, 1 mM EDTA) was added, and one time of phenol/chloroform extraction and one time of chloroform extraction followed by ethanol precipitation were conducted to concentrate and separate the included DNA molecules. After the DNA precipitate was dissolved into 10.5 µl of distilled water, the labeling reaction was conducted through incubation at 37° C. for 30 min in 10 mM Tris-HCl pH 7.5, 5 mM MgCl$_2$, 7.5 mM dithiothreitol, 4 units of Klenow fragment, 0.02 mM [α-$^{32}$P]dCTP, 0.02 mM dGTP, 0.02 mM dATP and 0.02 mM dTTP. After 10 µl of TE buffering solution was added and excessive α-$^{32}$P dCTP was removed using G25 spin column, the half amount thereof was electrophoeased in an 1% agarose gel followed by ethidium bromide staining to record the gel as photographs. The result is shown in Lane 1 of FIG. 12(B). After then, the gel was placed on a filter paper and dried in a gel drier. Signals were detected by taking autoradiogram of the dried gel, and then recorded on a X-ray film. The result of agarose gel electrophoresis is shown in Lane 1 in FIG. 12(A).

As a comparative experiments, the followings were conducted. Lane M contains DNA size makers and the sizes are shown at the left side of the diagram. The size markers were λDNA digested with restriction enzyme HindIII and labeled with [γ-$^{32}$P]ATP at the 5' terminus. Lane 4 contains the target DNA used for this experiment, which was electrophorased as it was. Lane 2 shows the result from the same reaction as Lane 1 except for using reverse complementary deoxyoligonucleotide 9 (oligo 9). Lane 3 shows the result from the same reaction as Lane 1 except for conducting the reaction without addition of the deoxyoligonucleotide.

---

The sequence of oligo 8:

5'-gtcctccgat cgttgtcaga agtaagttgg ccgcagtgtt atcactcatg
gttatggcag cactgcataa ttctcttact gtcatgccat ccgtaagatg
cttttctgtg actggtgagt-3'                (SEQ ID NO: 8)

-continued

The sequence of oligo 9:

5'-actcaccagt cacagaaaag catcttacgg atggcatgac
agtaagagaa ttatgcagtg ctgccataac catgagtgat aacactgcgg
ccaacttact tctgacaacg atcggaggac-3' (SEQ ID NO: 9)

Figure 12A:
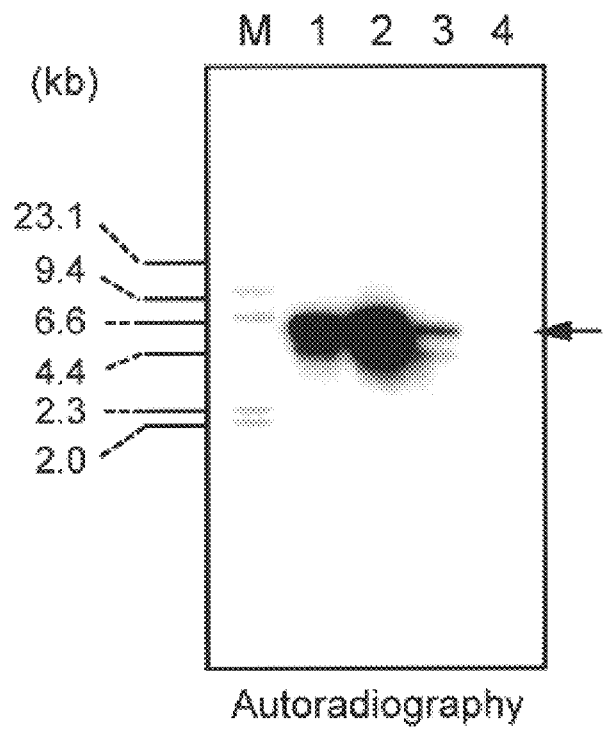
FIG. 12 is an autoradiograph (A) and a photograph (B) showing electrophoretical behavior on a gel submitted to autoradiography or stained with ethidium bromide after agarose gel electrophoresis, as conducted in Example 9.
Figure 12B:
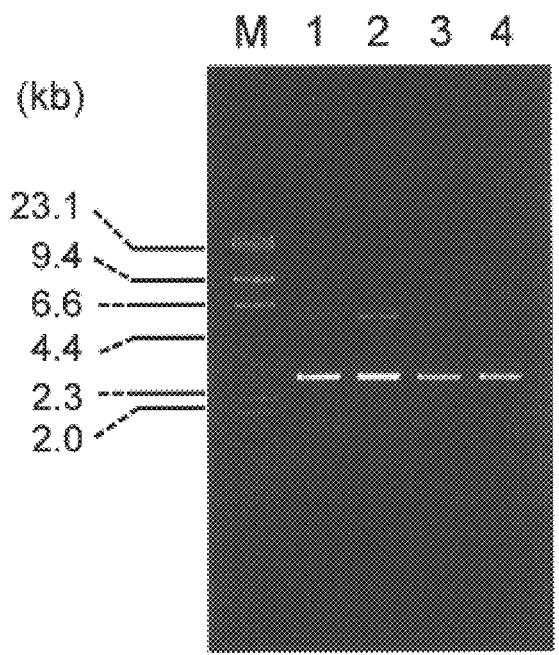

According to FIGS. 12(A) and (B), as shown in Lane 1 and 2, because the triple-strands formed are stably maintained, it is proven that labels can be incorporated into ant part of regions by using a circular DNA as the target DNA.

EXAMPLE 10

The Status of the Deoxyoligonucleotide After the Labeling Reaction

M13 mp18 RF DNA digested with restriction enzyme SnaB I to make it straight as the target and deoxyoligonucleotide 3 (oligo 3) of 60-mer having the sequence at the terminal region of the target DNA were prepared. The deoxyoligonucleotide had been labeled with [γ-$^{32}$P]ATP at its 5' terminus in advance. For triple-strand formation reaction between the target DNA and deoxyoligonucleotide 3 (oligo 3), two Reaction solutions A (20 μl) and B (20 μl) were prepared. Reaction solution A contains 1 pmol deoxyoligonucleotide 1 (oligo 1), 6.0 μg recA protein, 0.48 mM ATP-γS, 30 mM Tris-acetate (pH 7.2) and 2.5 mM magnesium acetate. Reaction solution B contains 200 ng target DNA, 0.48 mM ATP-γS, 30 mM Tris-acetate (pH 7.2) and 2.15 mM magnesium acetate.

After incubating Reaction solutions A and B individually at 37° C. for 15 min, the two were mixed and further incubated at 37° C. for 30 min. To 40 μl of the reaction solution at this time after triple-strand formation reaction, 0.5% (w/v) SDS, 0.7 mg/ml Proteinase K were added and incubated at 37° C. for 10 min for recA removal treatment. After then, 60 μl of TE buffering solution (10 mM Tris-HCl, 1 mM EDTA) was added to 100 μl, and one time of phenol/chloroform extraction and one time of chloroform extraction followed by ethanol precipitation were conducted to concentrate and separate the included DNA molecules. After the DNA precipitate was dissolved into 10.5 μl of distilled water, the incorporation reaction was conducted through incubation at 37° C. for 30 min in 10 mM Tris-HCl pH 7.5, 5 mM MgCl$_2$, 7.5 mM dithiothreitol, 4 units of Klenow fragment, 0.02 mM dCTP, 0.02 mM dGTP, 0.02 mM dATP and 0.02 mM dTTP. After the reaction was completed, 0.5% (w/v) SDS, 0.7 mg/ml Proteinase K were added and by incubating at 37° C. for 10 min, protein removal treatment was conducted. The half amount thereof was electrophorased in an 1% agarose gel followed by ethidium bromide staining to record the gel as photographs. The result is shown in Lane 1 of FIG. 13(B). After then, the gel was placed on a filter paper and dried in a gel drier. Signals were detected by taking autoradiogram of the dried gel and recorded on a X-ray film. The result is shown in Lane 2 in FIG. 13(A).

As a comparative experiments, the followings were conducted. Lane M contains DNA size makers and the sizes are shown at the left side of the diagram. The size markers were λDNA digested with restriction enzyme HindIII and labeled with [γ-$^{32}$P]ATP at the 5' terminus. Lane 1 contains the sample from the same triple-strand formation reaction as Lane 2 followed by electrophoresis without conducting the incorporation reaction. Lane 3 shows the result from the same triple-strand formation reaction as Lane 2 followed by the incorporation reaction conducted without addition of the four types of dNTPs. Lane 4 shows the result from the same triple-strand formation reaction as Lane 2 followed by the incorporation reaction conducted without addition of dATP. Lane 5 shows the result from the same triple-strand formation reaction as Lane 2 followed by the incorporation reaction conducted without addition of dATP.

Figure 13A:
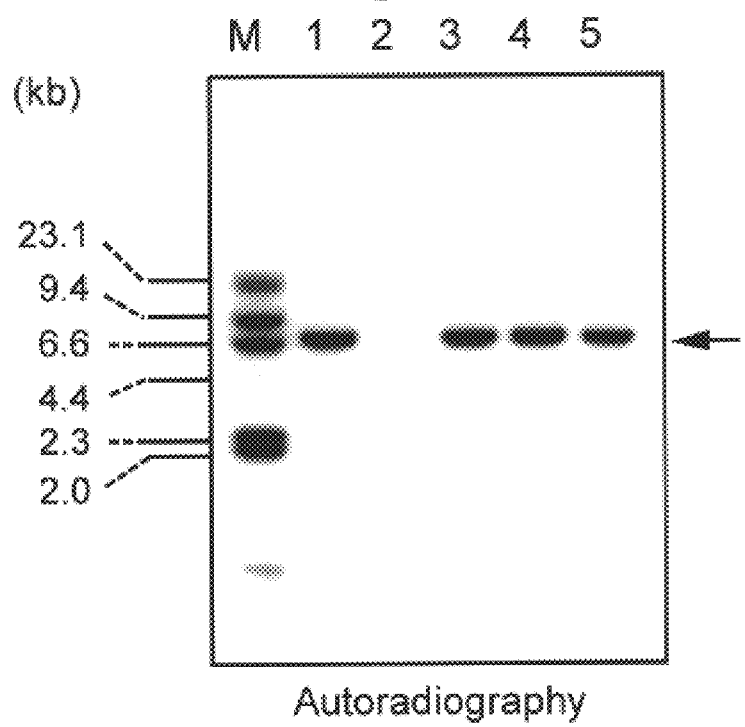
FIG. 13 is an autoradiograph (A) and a photograph (B) showing electrophoretical behavior on a gel submitted to autoradiography or stained with ethidium bromide after agarose gel electrophoresis, as conducted in Example 10.
Figure 13B:
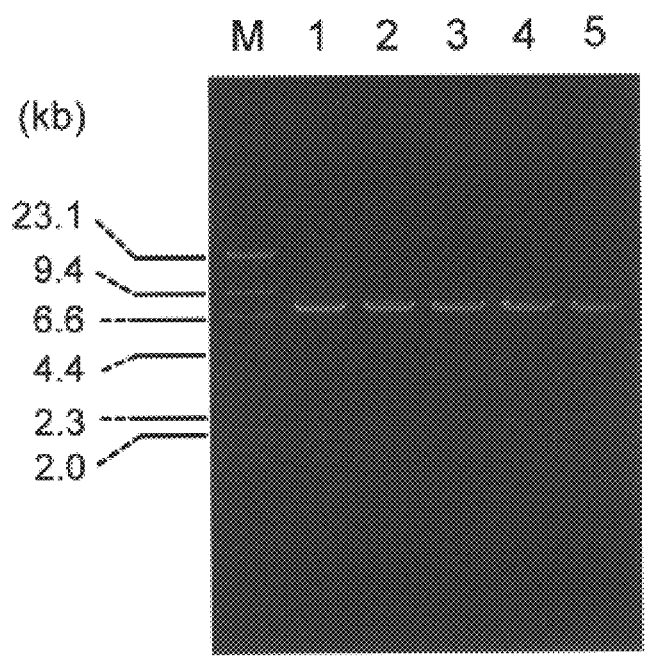

According to FIGS. 13(A) and (B), as shown in Lane 2, it is proven that the deoxyoligonucleotide used for the triple-strand formation is detached from the target DNA after the incorporation reaction of the four types of dNTPs using the DNA polymerase.

EXAMPLE 11

Reproducibility of the Labeling Reaction

The sample from the same reaction as Lane 1 of FIG. 5 (A) but before the electrophoresis was subjected to one time of phenol-chloroform extraction and one time of chloroform extraction followed by ethanol precipitation to concentrate and separate the DNA molecules included. Thus obtained DNA was used as the target DNA to conduct triple-strand formation reaction with deoxyoligonucleotide 3 (oligo 3). For the reaction, two Reaction solutions A (20 μl) and B (20 μl) were prepared. Reaction solution A contains 1 pmol deoxyoligonucleotide 3 (oligo 3), 6.0 μg recA protein, 0.48 mM ATP-γS, 30 mM Tris-acetate (pH 7.2) and 2.5 mM magnesium acetate. Reaction solution B contains 200 ng target DNA, 0.48 mM ATP-γS, 30 mM Tris-acetate (pH 7.2) and 2.15 mM magnesium acetate.

After incubating Reaction solutions A and B individually at 37° C. for 15 min, the two were mixed and further incubated at 37° C. for 30 min. To 40 μl of the reaction solution at this time after triple-strand formation, 0.5% (w/v) SDS, 0.7 mg/ml Proteinase K were added and incubated at 37° C. for 10 min to conduct recA removal treatment. After then, 60 μl of TE buffering solution (10 mM Tris-HCl, 1 mM EDTA) was added to 100 μl, and one time of phenol/chloroform extraction and one time of chloroform extraction followed by ethanol precipitation were conducted to concentrate and separate the included DNA molecules. After the DNA precipitate was dissolved into 10.5 μl of distilled water, the incorporation reaction was conducted through incubation at 37° C. for 30 min in 10 mM Tris-HCl pH 7.5, 5 mM MgCl$_2$, 7.5 mM dithiothreitol, 4 units of Klenow fragment, 0.02 mM dCTP, 0.02 mM dGTP, 0.02 mM DATP and 0.02 mM dTTP. After the reaction was completed, 0.5% (w/v) SDS, 0.7 mg/ml Proteinase K were added and by incubating it at 37° C. for 10 min, protein removal treatment was conducted. The half amount thereof was electrophorased in an 1% agarose gel followed by ethidium bromide staining to record the gel as photographs. The result is shown in FIG. 14(B). After then, the gel was placed on a filter paper and dried in a gel drier. Signals were detected by taking autoradiogram of the dried gel, and then recorded on a X-ray film. The result is shown in Lane 1 of FIG. 14(A). Lane 2 shows the result from the same reaction as Lane 1 conducted without addition of the DNA polymerase in the incorporation reaction. Lane 3 shows the result from the same reaction as Lane 1 conducted without addition of the four types of dNTPs in the incorporation reaction. Lane 4 shows the result from the same reaction as Lane 1 conducted only with addition of dCTP in the incorporation reaction.

Figure 14A:
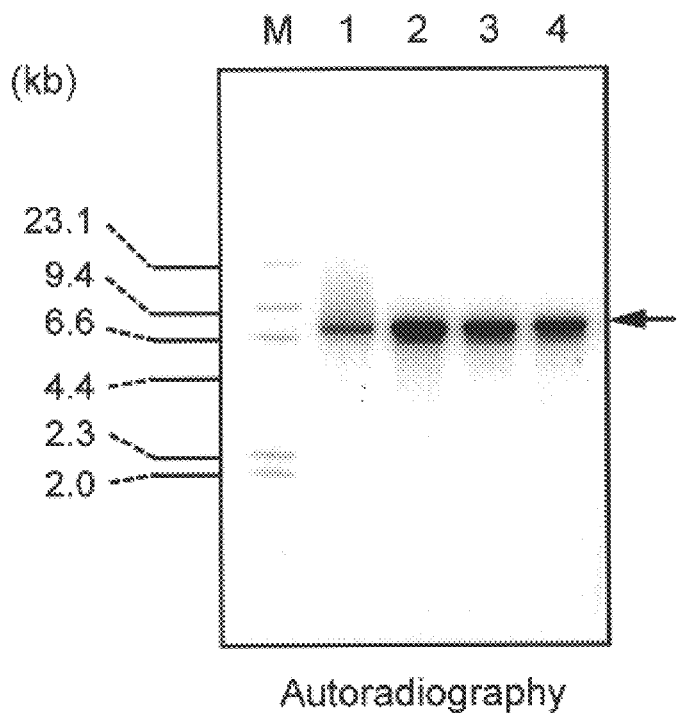
FIG. 14 is an autoradiograph (A) and a photograph (B) showing electrophoretical behavior on a gel submitted to autoradiography or stained with ethidium bromide after agarose gel electrophoresis, as conducted in Example 11.
Figure 14B:
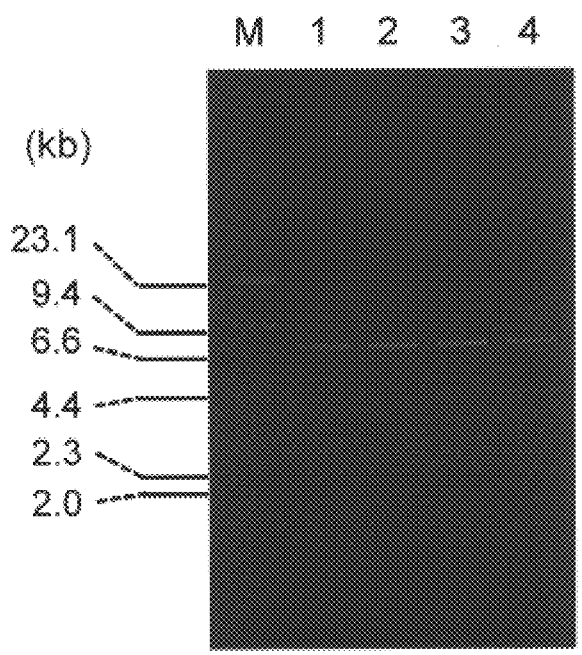

According to FIGS. 14(A) and (B), because the labels incorporated into the target DNA by the labeling reaction are expelled by conducting the incorporation reaction in the dNTPs in the series of the reactions according to the invention which are repeatedly conducted, reproducibility or a certain feature of a biological reaction is proved for the reaction.

EXAMPLE 12

Dependency of the Individual Reaction Components in the Triple-strand Formation Reaction M13 mp18 RF DNA digested with restriction enzyme SnaB I to make it straight as the target and deoxyoligonucleotide 3 (oligo 3) of 60-mer having the sequence at the terminal region of the target DNA were prepared. The deoxyoligonucleotide had been labeled with [γ-$^{32}$P]ATP at its 5' terminus. For triple-strand formation reaction between the target DNA and deoxyoligonucleotide 3 (oligo 3), two Reaction solutions A (20 μl) and B (20 μl) were prepared. Reaction solution A contains 1 pmol deoxyoligonucleotide 3 (oligo 3), 6.0 μg recA protein, 0.48 mM ATP-γS, 30 mM Tris-acetate (pH 7.2) and 2.5 mM magnesium acetate. Reaction solution B contains 200 ng target DNA, 0.48 mM ATP-γS, 30 mM Tris-acetate (pH 7.2) and 2.15 mM magnesium acetate.

After incubating Reaction solutions A and B individually at 37° C. for 15 min, the two were mixed and further incubated at 37° C. for 30 min. To 40 μl of the reaction solution at this time after triple-strand formation, 0.5% (w/v) SDS, 0.7 mg/ml Proteinase K were added and incubated at 37° C. for 10 min to conduct recA removal treatment. The half amount thereof was electrophorased in an 1% agarose gel followed by ethidium bromide staining to record the gel as photographs. The result is shown in FIG. 15(B). After then, the gel was placed on a filter paper and dried in a gel drier. Signals were detected by taking autoradiogram of the dried gel, then recorded on a X-ray film. The result is shown in Lane 1 in FIG. 15(A).

As a comparative experiments, the followings were conducted. Lane M contains DNA size makers and the sizes are shown at the left side of the diagram. The size markers were λDNA digested with restriction enzyme HindIII and labeled with [γ-$^{32}$P]ATP at the 5' terminus. Lane 2 shows the result from the same reaction as Lane 1 except for conducting the reaction without addition of recA. Lane 3 shows the result from the same reaction as Lane 1 except for conducting the reaction without addition of ATP-γS. Lane 4 shows the result from the same reaction as Lane 1 except for conducting the reaction using reverse complementary deoxyoligonucleotide 4 (oligo 4). Lane 5 shows the result from the same reaction as Lane 1 except for conducting the reaction using reverse homologous deoxyoligonucleotide 10 (oligo 10). Lane 6 shows the result from the same reaction as Lane 1 except for conducting the reaction using deoxyoligonucleotide 1 (oligo 1). Lane 7 contains the electrophorased sample from the reaction using deoxyoligonucleotide 1 (oligo 1) directing to pBR322 DNA digested with restriction enzyme Sca I as the target DNA. Lane 7 shows the result from the same reaction as Lane 1 except for using pBR322 DNA digested with restriction enzyme Sca I as the target DNA and labeled deoxyoligonucleotide 6 (oligo 6) having the sequence at the terminal region.

The sequence of oligo 10:

5'-tctccgaaac tcctgatttc tgaaaaagta ctccttcaaa ggtaatttgc ccattttatg-3'     (SEQ ID NO: 10)

Figure 15A:
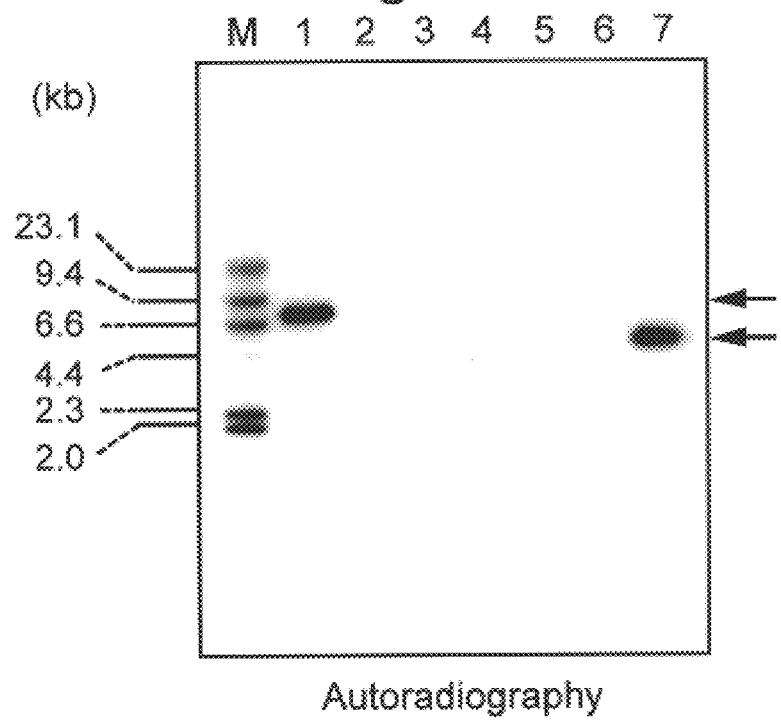
FIG. 15 is an autoradiograph (A) and a photograph (B) showing electrophoretical behavior on a gel submitted to autoradiography or stained with ethidium bromide after agarose gel electrophoresis, as conducted in Example 12.
Figure 15B:
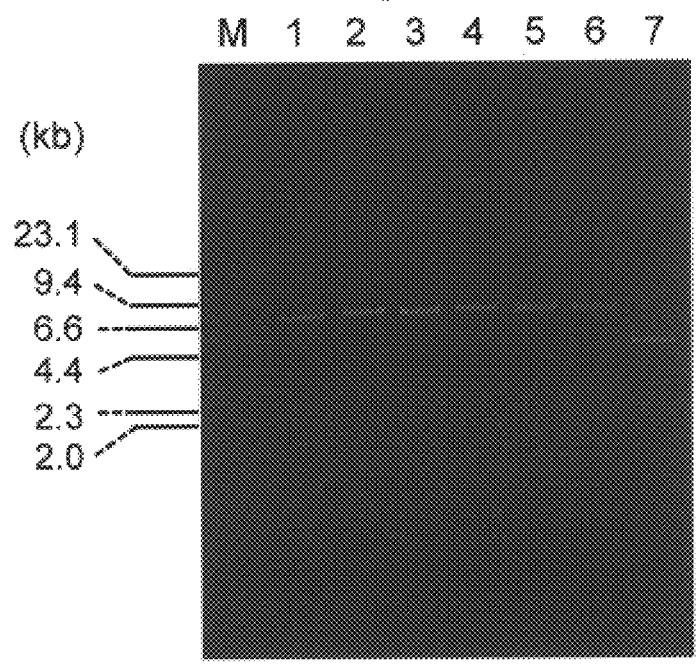

As shown in Lane 1 of FIG. 15(A), all the reaction components for the foundation of the reaction in Lane 1 are needed to be added to the reactant for the triple-strand formation reaction to occur. Moreover, because the triple-strand was not formed with the reverse complementary deoxyoligonucleotide and reverse homologous deoxyoligonucleotide, it is proven that the alternative orientation of the deoxyoligonucleotides is essential for the reaction.

EXAMPLE 13

Figure 16A:
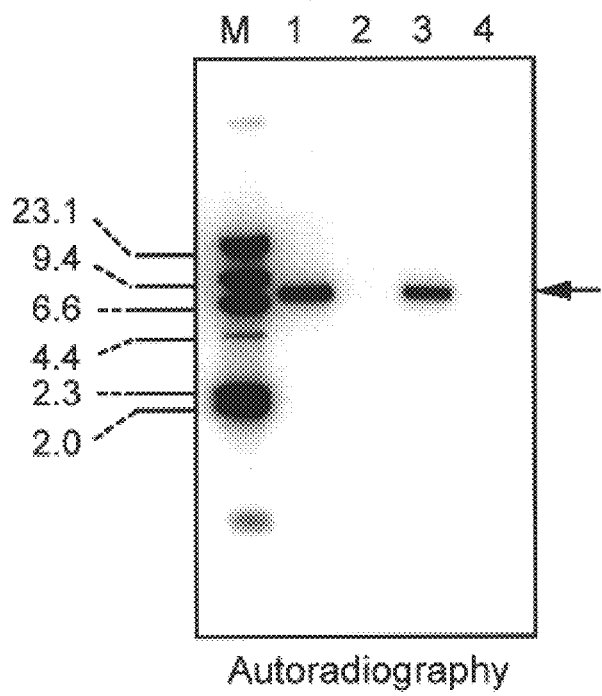
FIG. 16 is an autoradiograph (A) and a photograph (B) showing electrophoretical behavior on a gel submitted to autoradiography or stained with ethidium bromide after agarose gel electrophoresis, as conducted in Example 13.
Figure 16B:
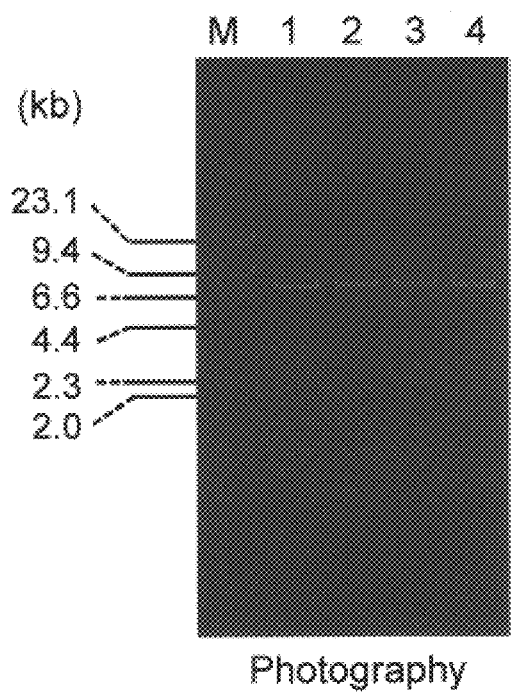

Sequence Orientation of Deoxyoligonucleotides Using in the Triple-strand Formation Reaction Lane 1 of FIG. 16(A) shows the result from the same reaction as Lane 1 of FIG. 15(A). Lane 2 shows the result from the same reaction as Lane 1 except for using labeled deoxyoligonucleotide 4 (oligo 4) having a reverse complementary sequence. Lane 3 shows the result from the same reaction as Lane 1 except for using labeled deoxyoligonucleotide 7 (oligo 7). Lane 4 shows the result from the same reaction as Lane 1 except for using labeled deoxyoligonucleotide 11 (oligo 11). (B) is the whole picture of the stained DNA on the same agarose gel as (A).

The sequence of oligo 11:

5'-gtaatgccac tacgaaggca ccaacctaaa acgaaagagg cgaagaata cactaaaaca-3'     (SEQ ID NO: 11)

According to FIGS. 16(A) and (B), the triple-strand formation can be conducted at both terminal regions of the straight target double-stranded DNA, and it is proven that the deoxyoligonucleotide to be used for the reaction needs to be of a homologous sequence having one of the orientations of both terminal regions of the target double-stranded DNA.

EXAMPLE 14

Change in Length of Deoxyoligonucleotides

Figure 17A:
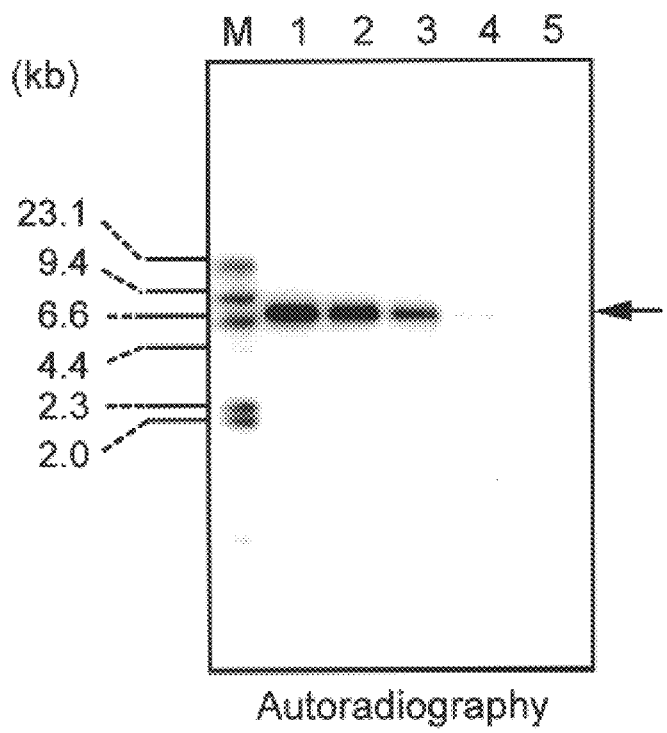
FIG. 17 is an autoradiograph (A) and a photograph (B) showing electrophoretical behavior on a gel submitted to autoradiography or stained with ethidium bromide after agarose gel electrophoresis, as conducted in Example 14.
Figure 17B:
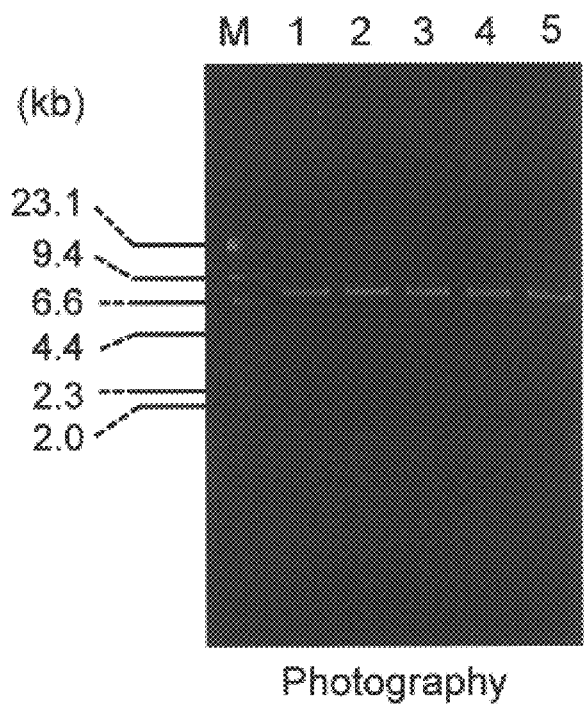

Lane 1 of FIG. 17(A) shows the result from the same reaction as Lane 1 of FIG. 15(A). Lane 2 shows the result from the same reaction as Lane 1 except for using labeled deoxyoligonucleotide 12 (oligo 12) where the 10-mer at the 5' terminal region is deleted from the deoxyoligonucleotide used in Lane 1. Lane 3 shows the result from the same reaction as Lane 1 except for using labeled deoxyoligonucleotide 13 (oligo 13) where the 20-mer at the 5' terminal region is deleted from the deoxyoligonucleotide used in Lane 1. Lane 4 shows the result from the same reaction as Lane 1 except for using labeled deoxyoligonucleotide 14 (oligo 14) where the 30-mer at the 5' terminal region is deleted from the deoxyoligonucleotide used in Lane 1. Lane 5 shows the result from the same reaction as Lane 1 except for using labeled deoxyoligonucleotide 15 (oligo 15) where the 40-mer at the 5' terminal region is deleted from the deoxyoligonucleotide used in Lane 1. (B) is the whole picture of the stained DNA on the same agarose gel as (A).

The sequence of oligo 12:

5'-aggactaaag acttttcat gaggaagttt ccattaaacg
ggtaaaatac-3' (SEQ ID NO: 12)

The sequence of oligo 13:

5'-actttttcat gaggaagttt ccattaaacg
ggtaaaatac-3' (SEQ ID NO: 13)

The sequence of oligo 14:

5'-gaggaagttt ccattaaacg ggtaaaatac-3'
(SEQ ID NO: 14)

The sequence of oligo 15:

5'ccattaaacg ggtaaaatac-3'
(SEQ ID NO: 15)

According to FIGS. (A) and (B), it is proven that the length of deoxyoligonucleotides to secure triple-strand formation is 30-mer or longer. Moreover, triple-strand formation efficiency is proven to be higher with longer deoxyoligonucleotides.

EXAMPLE 15

Figure 18A:
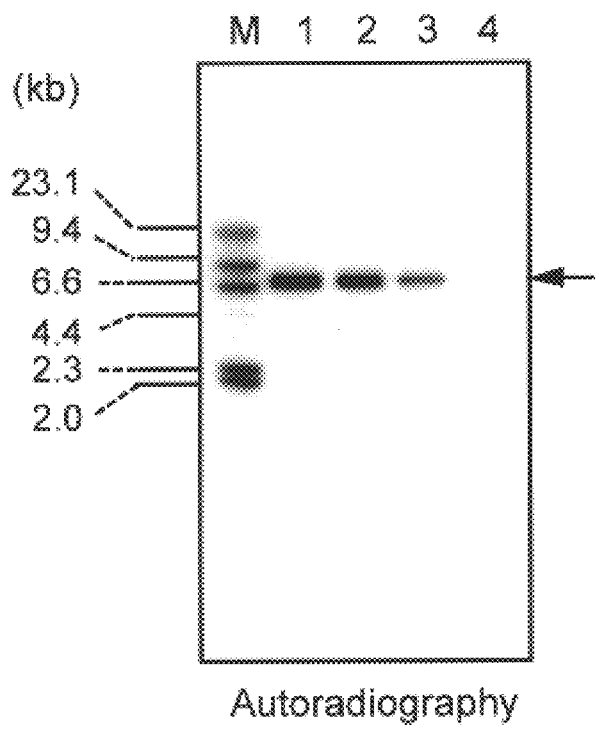
FIG. 18 is an autoradiograph (A) and a photograph (B) showing electrophoretical behavior on a gel submitted to autoradiography or stained with ethidium bromide after agarose gel electrophoresis, as conducted in Example 15.
Figure 18B:
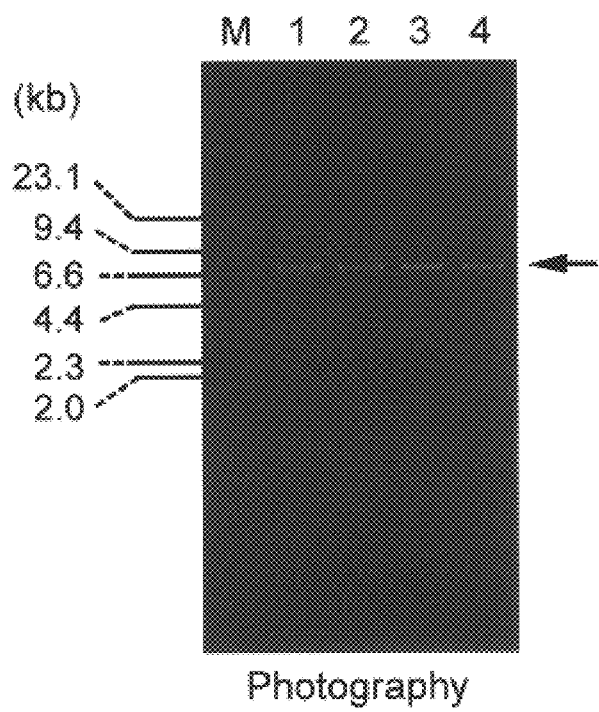

Relative Location of Deoxyoligonucleotide Sequences Essential for the Triple-strand Formation Reaction Lane 1 of FIG. 18(A) shows the result from the same reaction as Lane 1 of FIG. 15(A). Lane 2 shows the result from the same reaction as Lane 1 except for using deoxyoligonucleotide 16 (oligo 16) having the terminal region excluding the terminal 10-mer of the target DNA. Lane 3 shows the result from the same reaction as Lane 1 except for using deoxyoligonucleotide 17 (oligo 17) having the terminal region excluding the terminal 20-mer of the target DNA. Lane 4 shows the result from the same reaction as Lane 1 except for using deoxyoligonucleotide 18 (oligo 18) having the terminal region excluding the terminal 30-mer of the target DNA. (B) is the whole picture of the stained DNA on the same agarose gel as (A).

The sequence of oligo 16:

5'-caacggctac agaggctttg aggactaaag acttttcat gaggaagttt
ccattaaacg-3' (SEQ ID NO: 16)

The sequence of oligo 17:

5'-acgagggtag caacggctac agaggctttg aggactaaag acttttcat
gaggaagttt-3' (SEQ ID NO: 17)

The sequence of oligo 18:

5'-cagcatcgga acgagggtag caacggctac agaggctttg
aggactaaag acttttcat-3' (SEQ ID NO: 18)

According to FIGS. 18(A) and (B), the deoxyoligonucleotides essential for triple-strand formation need to locate on the region at least including the 20-mer from the terminus of the target DNA or on the region covering the terminus of the straighten target DNA. Still, when using an deoxyoligonucleotide having the sequence expanding to the terminus or covering the whole terminus of the straighten target DNA, triple-strand formation efficiency is proven to be higher.

EXAMPLE 16

Thermostability of Deoxyoligonucleotides in the Triple-strand Formation Reaction Lane 1 of FIG. 19 shows the result from electrophoresis of the same reaction as Lane 1 of FIG. 15(A) conducted using 10 µl sample to which 20 mM NaCl was added and which is then subjected to heat treatment (37° C., min). Lane 2 shows the result from the sample subjected to heat treatment (45° C., 10 min). Lane 3 shows the result from the sample subjected to heat treatment (55° C., 10 min). Lane 4 shows the result from the sample subjected to heat treatment (65° C., 10 min). Lane 5 shows the result from the sample subjected to heat treatment (75° C., 10 min). Lane 6 shows the result from the sample subjected to heat treatment (85° C., 10 min). (B) is the whole picture of the stained DNA on the same agarose gel as (A). (C) shows the result from the same reaction as (A) conducted using deoxyoligonucleotide 20 (oligo 20) with the length of 20-mer having the sequence at the terminal region of the target DNA digested with restriction enzyme SnaB I. (D) is the whole picture of the stained DNA on the same agarose gel as (C). These are all shown in FIG. 19.

The sequence of oligo 19:

5'-actttttcat gaggaagttt ccattaaacg
ggtaaaatac-3' (SEQ ID NO: 19)

According to FIG. 19, it is proven that the upper limitations for temperatures to maintain thermostability of the triple-strand formed using the deoxyoligonucleotide of 60-mer and the deoxyoligonucleotide of 40-mer are approximately 85° C. and 75° C., respectively. It is shown that when using deoxyoligonucleotide with its length of 60-mer or longer, thermostability of triple-strand becomes larger.

EXAMPLE 17

Immobilization of Labeled Nucleic Acids onto Magnetic Beads

The same reaction as Lane 1 of FIG. 5(A) was conducted except that the labeling reaction was conducted through incubation in 30 µl of a reaction solution containing 10 mM Tris-HCl, pH 7.5, $MgCl_2$, 7.5 mM dithiothreitol, 2 unit Klenow fragment, 0.2 mM biotin-11-dCTP, 0.2 mM dGTP, 0.2 mM dATP and 0.2 mM dTTP at 37° C. for 30 min. The sample before electrophoresis was immobilized onto streptoavidin beads (Dynabeads M-280 Streptavidin) was conducted as follows.

Twenty-five µl (a 10 µg/µl stock solution) of Dynabeads was washed once with 100 µl 6×SSC (0.5 M sodium chloride, 0.05 M sodium citrate) followed by suspending in 30 µl of the above-mentioned reaction solution. After standing it at room temperature for 30 min, Dynabeads were collected with Magnetic particle concentrator. After washing it twice with 100 µl TE buffering solution (10 mM Tris-HCl, 1 mM EDTA), it was suspended in 100 µl alkaline denaturing solution (0.125 M NaOH, 0.1 M NaCl) and stood at room temperature for five min. The washing treatment with the alkaline denaturing solution was repeated further three times. After washing four times with 100 µl TE buffering solution, it was suspended in 25 µl TE buffering solution. PCR was used to confirm whether DNA is attached onto a solid phase and further whether the whole length of the DNA is attached.

PCR was conducted using 5 µl of the suspension solution of Dynabeads as the template in 50 µl of the reaction solution. Primer 1 which is a 35-mer at one terminus of M13 mp18 RF DNA and primer 2 which is a 35-mer at another terminus of M13 mp18 RF DNA were used as the primers for PCR where 27 cycles (98° C.-20 sec, 68° C.-5 min) were conducted according to conventional arts. A part of the PCR products was electrophoresed in an 1% agarose gel, and then the gel was stained with ethidium bromide to record photographs of the gel.

Figure 20:
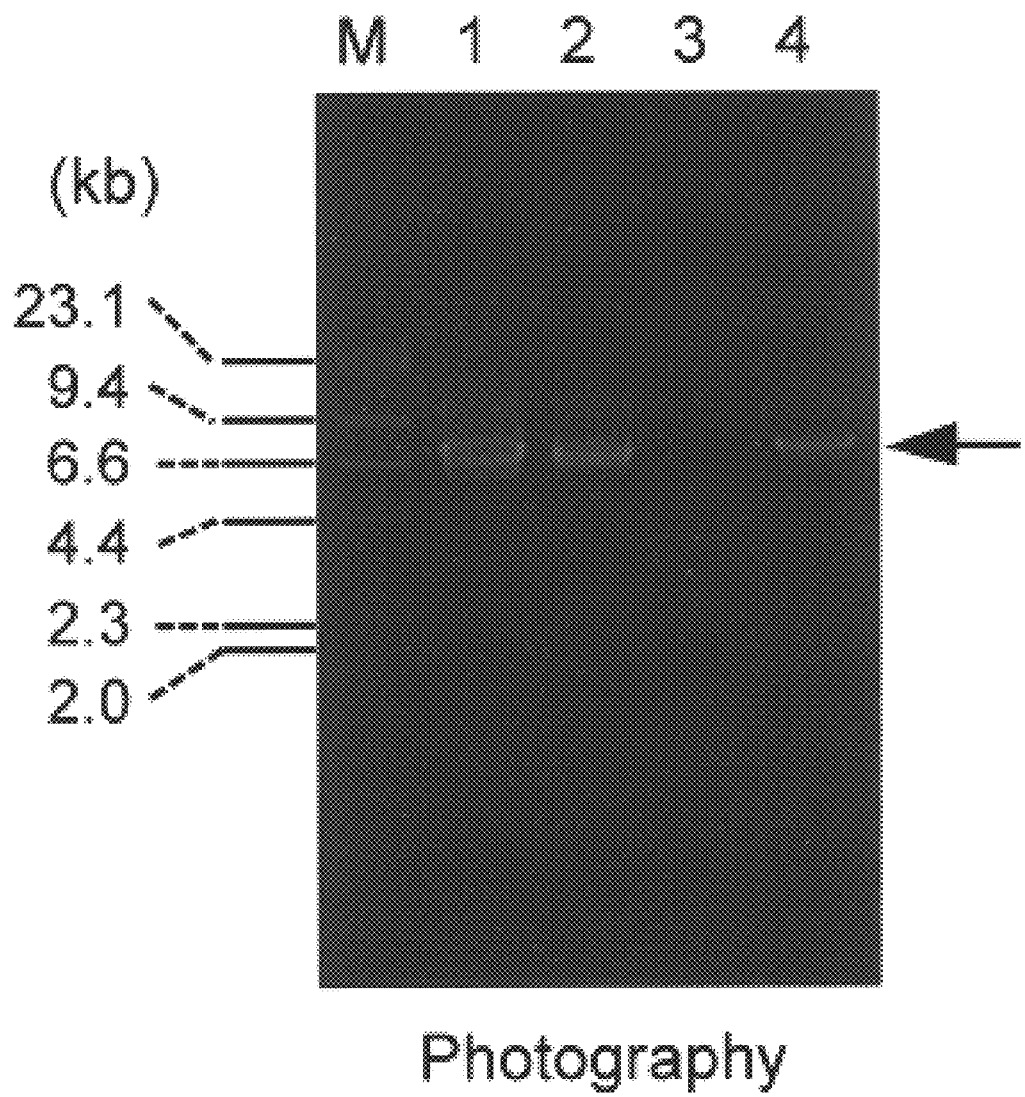
FIG. 20 is a photograph showing electrophoretical behavior on a gel stained with ethidium bromide after agarose gel electrophoresis, as conducted in Example 17.

The result is shown in FIG. 20. Lane 2 contains the sample from the same reaction as Lane 1 using M13 mp18 RF DNA digested with restriction enzyme SnaB I as the target DNA and deoxyoligonucleotide 6 (oligo 6) having the sequence at another terminal region of the SnaB I-digested 13mp18RF DNA. Lane 3 shows the result from the same reaction as Lane 1 conducted without addition of the deoxyoligonucleotide. Lane 4 contains the sample after PCR where M13 mp18 RF DNA digested with restriction enzyme SnaB I as the target DNA was used as the template, which is derived from the size makers of the PCR products. Moreover a part thereof was subcloned to pGEM-T vector (manufactured by Promega Inc.) before the basic sequences of the 40 clones containing the insert were decided at their terminal regions of the target DNA.

Primer 1: 5'-gtattttacccgtttaatggaaacttcctcatgaa-3' (SEQ ID NO: 20)

Primer 2: 5'-gtaatgccactacgaaggcaccaacctaaaacgaa-3' (SEQ ID NO: 21)

According to FIG. 20, it is proven that the biotin-labeled nucleotide is incorporated into the target DNA by the reaction, and then the target DNA incorporating the biotin binds the streptoavidin-coated magnetic beads. Moreover, the basic sequence of the labeled target DNA is proved to be substantially same as that of the target DNA before the reaction.

EXAMPLE 18

A Device for Analytical Measurement of Biomolecular Interaction Example Use of IAsys Manufactured by Affinity Sensors Inc.

At the first, the biotin-labeled DNA immediately before binding beads was prepared by the same reaction as Lane 1 of FIG. 20(A). The above-mentioned labeled nucleic acid was immobilized onto the biotin-bound IAsys sensor surface (biotin-bound IAsys cuvette) for measurement in IAsys in the following way.

(a) Washing of cuvette: 200 µl of 1×PBS-T solution (100 mM Tris-HCl pH 7.5, 150 mM CaCl$_2$, 0.05% Tween 20) was injected and washed five times.

(a) Binding of streptoavidin: 100 µl of 1 mg/ml streptoavidin was injected and stood at 25° C. for 30 min.

(a) Removal of unreacted streptoavidin: 200 µl of 1×PBS-T solution was injected and washed five times.

(a) Immobilization of nucleic acids: To above-mentioned biotin-labeled nucleic acid solution, PBS-T solution was added to 100 µl, the final concentration thereof being 1×concentration, which then was injected into a cuvette and stood at 25° C. for 30 min.

(a) Removal of non-reacted nucleic acids: 200 µl of 1×PBS-T solution was injected and washed five times.

(b) Denaturation treatment of double-stranded nucleic acids: 100 µl of alkaline denaturing solution (0.125 M NaOH, 0.1 M NaCl) was injected and stood at 25° C. for 5 min. After injecting the alkaline denaturing solution further three times, it was washed with 200 µl of 6×SSC solution five times.

(c) Injection of a single-stranded DNA: In a cuvette where 100 µl of 6×SSC solution was placed in advance, 100 ng of a circular single-stranded DNA (M13 mp18 ssDNA) having the sequence complementary to the immobilized nucleic acids was injected and the association was measured with IAsys.

(d) Denaturation treatment of double-stranded nucleic acids: 100 µl of alkaline denaturing solution (0.125 M NaOH, 0.1 M NaCl) was injected and stood at 25° C. for 5 min. After injecting the alkaline denaturing solution further three times, it was washed with 200 µl of 6×SSC solution five times.

(e) Injection of a single-stranded DNA: In a cuvette where 100 µl of 6×SSC solution was placed in advance, 100 ng of a circular single-stranded DNA (φ×174 ssDNA) without the immobilized sequence was injected and the association was measured with IAsys.

(f) 100 ng of a circular single-stranded DNA (M13 mp18 ssDNA) having the sequence complementary to the immobilized nucleic acids was injected and the association was measured with IAsys.

Figure 21:
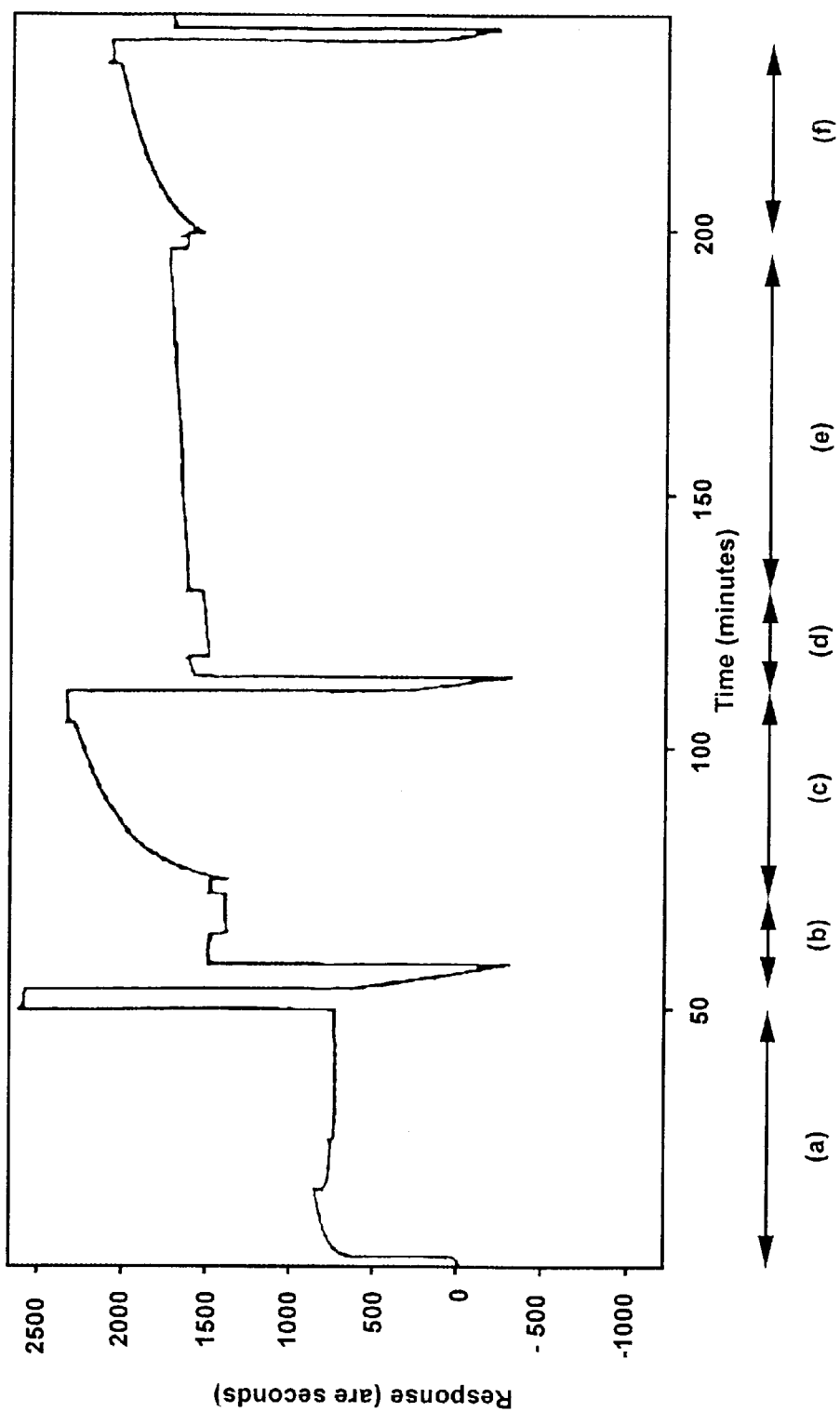
FIG. 21 in a graph showing data on immobilization of the target DNA onto the solid phase using a device for biomolecule-interaction analysis; IAsys mentioned in Example 18.

The results from a series of measurements above are shown in FIG. 21.

According to FIG. 21, by labeling the target DNA with a functional group, the DNA is confirmed to be tightly immobilized on a solid phase such as a censor surface. Moreover, because the immobilized double-stranded DNA is labeled only on its one strand of the DNA strand, it can be denatured into the single-stranded DNAs on the solid phase and then hybridization of a DNA complementary to the single-strands allows DNA detection.

SEQUENCE LISTING

<160> NUMBER OF SEQ ID NOS: 21

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence:It is
      synthesized referring to the nucleotide sequence
      at the 3' terminal side of pBR322 Sca I fragment.

<400> SEQUENCE: 1
cactgcataa ttctcttact gtcatgccat ccgtaagatg cttttctgtg actggtgagt    60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: It is
      synthesized as a reverse complementary strand of
      the nucleotide sequence at the 3' terminal side of
      pBR 322 Sca I fragment.

<400> SEQUENCE: 2
actcaccagt cacagaaaag catcttacgg atggcatgac agtaagagaa ttatgcagtg    60

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: It is
      synthesized referring to the nucleotide sequence
      at one of the terminal sides of the Sna BI
      fragment of phage vector M13 mp18 RF.

<400> SEQUENCE: 3
agaggctttg aggactaaag acttttttcat gaggaagttt ccattaaacg ggtaaaatac    60

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: It is
      synthesized as a reverse complementary strand of
      the nucleotide sequence at one of the terminal
      sides of the Sna BI fragment of phage vector M13
      mp18 RF.

<400> SEQUENCE: 4
gtattttacc cgtttaatgg aaacttcctc atgaaaaagt ctttagtcct caaagcctct    60

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: It is
      synthesized referring to the nucleotide sequence
      at one of the terminal sides of the Hnc II
      fragment of phage vector M13 mp18 RF.

<400> SEQUENCE: 5
ggaaacagct atgaccatga ttacgaattc gagctcggta cccggggatc ctctagagtc    60

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: It is
      synthesized referring to the nucleotide sequence
      at another terminal side of the Sna BI fragment of
      phage vector M13 mp18 RF.

<400> SEQUENCE: 6
tgttttagtg tattctttcg cctctttcgt tttaggttgg tgccttcgta gtggcattac    60

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: It is
      synthesized referring to the nucleotide sequence
      at one of the terminal sides of the Hinc II
      fragment of phage vector M13 mp18 RF.

<400> SEQUENCE: 7
ttacgaattc gagctcggta cccggggatc ctctagagtc                              40

<210> SEQ ID NO 8
<211> LENGTH: 120
<212> TYPE: DNA
<213> ORGANISM: Artificial Sequence
<220> FEATURE:
<223> OTHER INFORMATION: Description of Artificial Sequence: It is
      synthesized referring to the nucleotide sequence
      of circular pBR 322.

<400> SEQUENCE: 8
gtcctccgat cgttgtcaga agtaagttgg ccgcagtgtt atcactcatg gttatggcag       60
cactgcataa ttctcttact gtcatgccat ccgtaagatg cttttctgtg actggtgagt      120

<210> SEQ ID NO 9
<211> LENGTH: 120
<212> TYPE: DNA
<213> ORGANISM: Artificial Sequence
<220> FEATURE:
<223> OTHER INFORMATION: Description of Artificial Sequence: It is
      synthesized as a reverse complementary strand of
      the nucleotide sequence of circular pBR 322.

<400> SEQUENCE: 9
actcaccagt cacagaaaag catcttacgg atggcatgac agtaagagaa ttatgcagtg       60
ctgccataac catgagtgat aacactgcgg ccaacttact tctgacaacg atcggaggac      120

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: It is
      synthesized as a reverse complementary strand of
      the nucleotide sequence at one of the terminal
      sides of pBR 322 Sca I fragment.

<400> SEQUENCE: 10
tctccgaaac tcctgatttc tgaaaaagta ctccttcaaa ggtaatttgc ccattttatg       60

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: It is
      synthesized as a reverse complementary strand of
      the nucleotide sequence at one of the terminal
      sides of the Sca I fragment of phage vector M13
      mp18 RF.

<400> SEQUENCE: 11
gtaatgccac tacgaaggca ccaacctaaa acgaaagagg cgaaagaata cactaaaaca       60

```
<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: It is
      synthesized referring to the nucleotide sequence
      at one of the terminal sides of the Sca I fragment
      of phage vector M13 mp18 RF.

<400> SEQUENCE: 12
aggactaaag acttttcat gaggaagttt ccattaaacg ggtaaaatac              50

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: It is
      synthesized referring to the nucleotide sequence
      at one of the terminal sides of the Sca I fragment
      of phage vector M13 mp18 RF.

<400> SEQUENCE: 13 acttttcat gaggaagttt ccattaaacg ggtaaaatac                         40

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: It is
      synthesized referring to the nucleotide sequence
      at one of the terminal sides of the Sca I fragment
      of phage vector M13 mp18 RF.

<400> SEQUENCE: 14
gaggaagttt ccattaaacg ggtaaaatac                                   30

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: It is
      synthesized referring to the nucleotide sequence
      at one of the terminal sides of the Sca I fragment
      of phage vector M13 mp18 RF.

<400> SEQUENCE: 15
ccattaaacg ggtaaaatac                                              20

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: It is
      synthesized referring to the sequence at the
      terminal region excluding the terminal 10-mer of
      one of the terminal regions of the Sca I fragment
      of phage vector M13 mp18 RF.

<400> SEQUENCE: 16
caacggctac agaggctttg aggactaaag acttttcat gaggaagttt ccattaaacg   60

<210> SEQ ID NO 17
<211> LENGTH: 60
<212> TYPE: DNA
```

```
<213> ORGANISM: Artificial Sequence
<220> FEATURE:
<223> OTHER INFORMATION: Description of Artificial Sequence: It is
      synthesized referring to the sequence at the
      terminal region excluding the terminal 20-mer of
      one of the terminal regions of the Sca I fragment
      of phage vector M13 mp18 RF.

<400> SEQUENCE: 17
acgagggtag caacggctac agaggctttg aggactaaag acttttttcat gaggaagttt      60

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: It is
      synthesized referring to the sequence at the
      terminal region excluding the terminal 30-mer at
      one of the terminal sides of the Sca I fragment of
      phase vector M13 mp18 RF.

<400> SEQUENCE: 18
cagcatcgga acgagggtag caacggctac agaggctttg aggactaaag acttttttcat      60

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: It is
      synthesized referring to the nucleotide sequence
      at one of the terminal sides of the Sca I fragment
      of phage vector M13 mp18 RF.

<400> SEQUENCE: 19
actttttcat gaggaagttt ccattaaacg ggtaaaatac                              40

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: It is
      synthesized referring to the nucleotide sequence
      at one of the terminal sides of the Sna BI
      fragment of phage vector M13 mp18 RF.

<400> SEQUENCE: 20
gtattttacc cgtttaatgg aaacttcctc atgaa                                   35

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: It is
      synthesized referred to the nucleotide sequence at
      another terminal side of the Sna BI fragment of
      phage vector M13 mp18 RF.

<400> SEQUENCE: 21
gtaatgccac tacgaaggca ccaacctaaa acgaa                                   35
```

What is claimed is:

1. A method for preparing a labeled double-stranded DNA molecule by replacing a deoxyoligonucleotide sequence of a certain region of at least one of two single-stranded DNAs constituting a double-stranded DNA molecule with a deoxyoligonucleotide sequence having at least one labeled nucleotide, wherein the preparation method comprises the steps of:

(A) incubating at least one type of deoxyoligonucleotide molecule having a sequence substantially equivalent to a certain region of one strand of the double-stranded DNA molecule and the double-stranded DNA molecule under a condition wherein said deoxyoligonucleotide molecule and double-stranded DNA molecule form a triple-stranded DNA at the 3' terminal region or the non-terminal region in a single-stranded DNA of the double-stranded DNA, and (B) incubating at least one type of complex of the double-stranded DNA and said at least one deoxyoligonucleotide having a region of the triple-stranded DNA formed in step (A) in the presence of four types of dNTPs comprising at least one labeled dNTP under a condition wherein the deoxyoligonucleotide sequence of the certain region of one strand of the double-stranded DNA molecule in said complex is substituted with a labeled deoxyoligonucleotide sequence, wherein said labeled deoxyoligonucleotide sequence has at least one labeled nucleotide, creating a labeled double-stranded DNA.

2. The method according to claim 1, wherein the deoxyoligonucleotide sequence of a certain region exists at the 3' terminal side in a single-stranded DNA of the double-stranded DNA and one type of deoxyoligonucleotide having a sequence equivalent to the deoxyoligonucleotide sequence is used.

3. The method according to claim 1, wherein the deoxyoligonucleotide sequence of a certain region exists at a non-terminal region of the double-stranded DNA and one type of deoxyoligonucleotide having a sequence equivalent to the deoxyoligonucleotide sequence is used.

4. The method according to claim 1, wherein the condition where a triple-stranded DNA is formed in step (A) is a condition where by incubating in an aqueous solution comprising a homologous recombinant protein, and one or more type(s) of nucleotide triphosphate(s) or analogue(s) thereof selected from a group consisting of ATP, ATP-γS, dATP, UTP, dUTP, CTP, dCTP and GTP, a complex of said protein and said double-stranded DNA and deoxyoligonucleotide is formed.

5. The method according to claim 4, further comprising a step where the homologous recombinant protein is removed from the complex of said protein and the double-stranded DNA and deoxyoligonucleotide.

6. The method according to claim 4, wherein the homologous recombinant protein is selected from proteins of a group consisting of recA protein, recA-like proteins and modified recA proteins.

7. The method according to claim 5, wherein Proteinase K is present.

8. The method according to claim 1, wherein the condition in step (B) comprises an enzyme that is: DNA Polymerase I, Polymerase Klenow fragment (Klenow enzyme), DNA Polymerase I fragment (Exo nuclease minus), T4 DNA Polymerase or gene-modified polymerases thereof, T7 DNA Polymerase or gene-modified polymerases thereof, or various types of heat-resistant polymerases.

9. The method according to claim 1, wherein Klenow enzyme is present.

10. The method according to claim 1, wherein the deoxoligonucleotide used in step (A) consists of at least 15 mer.

11. The method according to claim 1, wherein the labeled dNTP is labeled with a label selected from a group consisting of radioisotopes and low molecular weight organic compounds.

12. The method according to claim 1, wherein the label is selected from a group consisting of $^{32}P$, $^{35}S$, $^{33}P$, $^{3}H$, biotin, fluorescein, digoxigenin, tetramethylrhodamin, alkaline phosphatase.

* * * * *